(12) United States Patent
Hubbard, Jr. et al.

(10) Patent No.: US 11,369,524 B2
(45) Date of Patent: Jun. 28, 2022

(54) ABSORBENT STRUCTURE

(71) Applicant: The Procter & Gamble Company, Cincinnati, OH (US)

(72) Inventors: Wade Monroe Hubbard, Jr., Wyoming, OH (US); Gerard A Viens, Wyoming, OH (US); Kelyn Anne Arora, Cincinnati, OH (US); Nathan Ray Whitely, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 523 days.

(21) Appl. No.: 15/843,655

(22) Filed: Dec. 15, 2017

(65) Prior Publication Data

US 2018/0168884 A1 Jun. 21, 2018

Related U.S. Application Data

(60) Provisional application No. 62/437,241, filed on Dec. 21, 2016, provisional application No. 62/437,259, filed on Dec. 21, 2016.

(51) Int. Cl.
*A61F 13/15* (2006.01)
*A61F 13/47* (2006.01)
(Continued)

(52) U.S. Cl.
CPC ........ *A61F 13/15731* (2013.01); *A61F 13/47* (2013.01); *A61F 13/531* (2013.01); *A61F 13/534* (2013.01); *A61F 13/53708* (2013.01); *B32B 5/022* (2013.01); *B32B 5/18* (2013.01); *B32B 5/245* (2013.01);
(Continued)

(58) Field of Classification Search
CPC ............. A61F 13/15731; A61F 13/531; A61F 13/534; A61F 13/53; A61F 2013/15829; A61F 13/53708; A61F 2013/530824; B24C 1/04; B32B 2266/06; B32B 5/18; B32B 5/265
See application file for complete search history.

(56) References Cited

U.S. PATENT DOCUMENTS 3,485,706 A * 12/1969 Evans ................... D04H 18/04
428/134
3,683,921 A * 8/1972 Brooks ............. A61F 13/00029
604/366

(Continued)

FOREIGN PATENT DOCUMENTS

CN 2863046 Y 1/2007

OTHER PUBLICATIONS

International Search Report dated Feb. 27, 2018, Application No. PCT/US2017/066944, 12 pages.

*Primary Examiner* — Michele M Kidwell
(74) *Attorney, Agent, or Firm* — William E. Gallagher; Andres E. Velarde

(57) ABSTRACT

An absorbent structure is disclosed. The absorbent structure includes a first fibrous layer having a first surface and a second surface and a second layer having a first surface and second surface. The first fibrous layer is substantially planar and the second absorbent layer includes voids within the layer. The absorbent structure first fibrous layer and the second layer exhibit a structural integrity substantially equal to an absorbent structure without voids.

16 Claims, 13 Drawing Sheets

(51) Int. Cl.

| | | |
|---|---|---|
| *A61F 13/531* | (2006.01) | |
| *B32B 5/02* | (2006.01) | |
| *B32B 5/18* | (2006.01) | |
| *B32B 5/24* | (2006.01) | |
| *A61F 13/537* | (2006.01) | |
| *A61F 13/534* | (2006.01) | |
| *B24C 1/04* | (2006.01) | |
| *A61F 13/53* | (2006.01) | |

(52) U.S. Cl.
CPC ........... *A61F 2013/15715* (2013.01); *A61F 2013/15829* (2013.01); *A61F 2013/53445* (2013.01); *A61F 2013/530824* (2013.01); *B24C 1/04* (2013.01); *B32B 2262/0253* (2013.01); *B32B 2266/025* (2013.01); *B32B 2266/06* (2013.01); *B32B 2555/02* (2013.01)

(56) References Cited

U.S. PATENT DOCUMENTS

| | | | | |
|---|---|---|---|---|
| 4,286,003 A * | 8/1981 | Higgins | ............... | B32B 5/26 428/95 |
| 5,397,316 A * | 3/1995 | LaVon | ............... | A61F 13/535 604/369 |
| 5,961,507 A | 10/1999 | Widlund | | |
| 6,429,351 B1 | 8/2002 | Guidotti et al. | | |
| 6,989,075 B1 * | 1/2006 | Kao | ............... | A61K 8/0208 162/125 |
| 8,137,338 B2 | 3/2012 | Pugsley et al. | | |
| 8,359,720 B2 * | 1/2013 | Dorsey | ............... | D04H 5/02 28/104 |
| 10,028,817 B2 | 7/2018 | Jagger et al. | | |
| 2003/0083631 A1 * | 5/2003 | Chen | ............... | A61F 13/47218 604/380 |
| 2005/0266230 A1 * | 12/2005 | Hill | ............... | B32B 5/30 428/317.9 |
| 2006/0246272 A1 * | 11/2006 | Zhang | ............... | B32B 5/18 428/304.4 |
| 2009/0148485 A1 | 6/2009 | Whitehead | | |
| 2014/0295135 A1 * | 10/2014 | Thompson, Jr. | ............... | B32B 3/266 428/138 |
| 2015/0313770 A1 * | 11/2015 | Hubbard, Jr. | ............... | A61F 13/534 604/369 |
| 2015/0313771 A1 * | 11/2015 | Bergstrom | ............... | A61F 13/53708 604/385.101 |
| 2015/0351976 A1 * | 12/2015 | Viens | ............... | D04H 1/46 604/378 |
| 2018/0169832 A1 * | 6/2018 | Viens | ............... | B24C 1/04 |
| 2019/0269564 A1 | 9/2019 | Zhang et al. | | |
| 2020/0306106 A1 | 10/2020 | Zhang et al. | | |
| 2020/0307149 A1 | 10/2020 | Zhang et al. | | |

\* cited by examiner

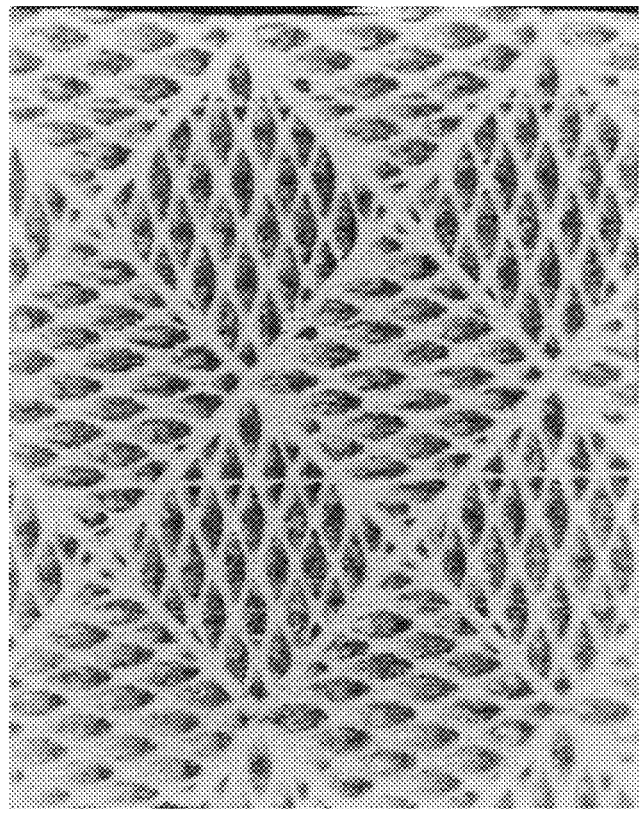
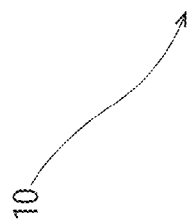
Fig. 6

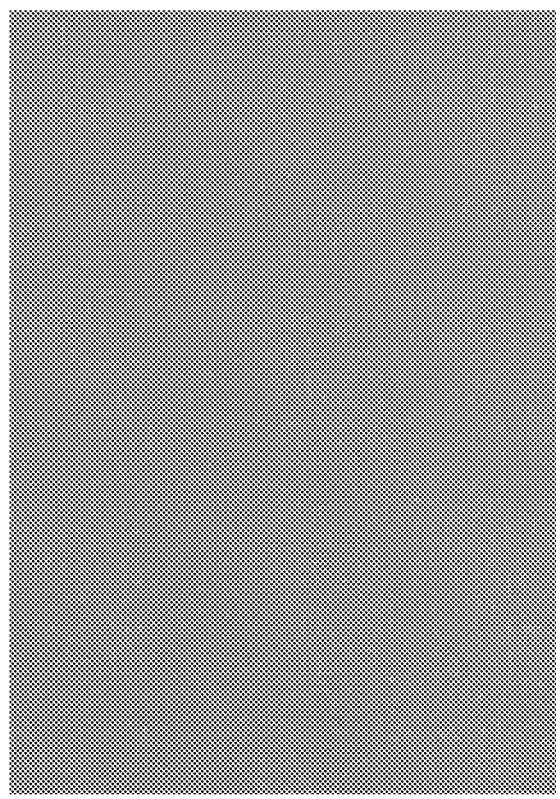
Fig. 8

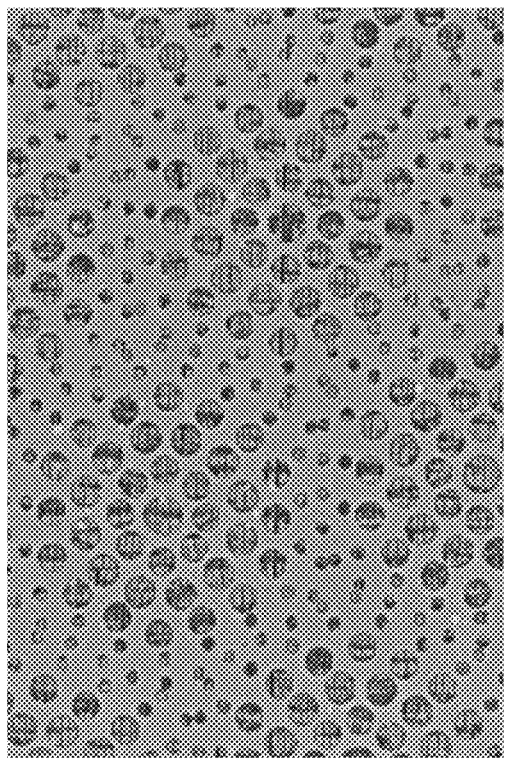
Fig. 11

ABSORBENT STRUCTURE

FIELD OF THE INVENTION

The present invention relates to a method of etching an absorbent structure by using a fluid. The absorbent structure is useful in absorbent articles such as diapers, incontinent briefs, training pants, diaper holders and liners, sanitary hygiene garments, and the like.

BACKGROUND OF THE INVENTION

One of the challenges in creating an absorbent core for an absorbent article is the placement of absorbent material in specific desired locations. Furthermore, once placed, the absorbent material should desirably stay in the chosen location. Traditionally, adhesives have been used to place the absorbent within a fixed volumetric space within the core. However, unless the adhesives are used to seal a pocket or channel, the absorbent material may move during use or once it is in contact with fluid. Additionally, the adhesive may inhibit absorption of fluids. In reference to foam cores, traditionally, foam is located throughout the core and then portions may be extracted using knife. These extractions or apertures are done using a knife and must cut through the entire section to extract entire pieces of the core. Alternatively, large manageable pieces may be placed on a laminate in some predetermined configuration. Cutting through the entire core may reduce the absorbent core integrity while the adding of large pieces represents no continuous system.

As such, there exists a need to create a method to reduce or remove absorbent material selectively within an absorbent structure without significantly impacting the absorbent structure's structural integrity. Additionally, there exists a need to reduce or remove absorbent material selectively within an absorbent core at a micro scale that allows for modifications of the core without necessitating the removal of significant portions of the core. Last, there exists a need for an absorbent structure wherein absorbent material has been reduced or removed selectively without having impacted the absorbent structure's structural integrity.

SUMMARY OF THE INVENTION

An absorbent structure is disclosed. The absorbent structure includes a first fibrous layer having a first surface and a second surface and a second layer having a first surface and second surface. The first fibrous layer is substantially planar and the second absorbent layer includes voids within the layer. The absorbent structure first fibrous layer and the second layer exhibit a structural integrity substantially equal to an absorbent structure without voids.

An absorbent structure is additionally disclosed. The absorbent structure includes a first fibrous layer having a first surface and a second surface and a second layer having a first surface and second surface. The first fibrous layer is substantially planar and the second absorbent layer comprises fissures within the layer. The absorbent structure first fibrous layer and the second layer exhibit a structural integrity substantially equal to an absorbent structure without fissures.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 6 is a top view of a portion of fluid etched absorbent layer.

FIG. 8 is a top view of a fluid etched absorbent structure.

FIG. 11 is a top view of the structure of FIG. 10 with a backlight.

DETAILED DESCRIPTION OF THE INVENTION

Figure 1:
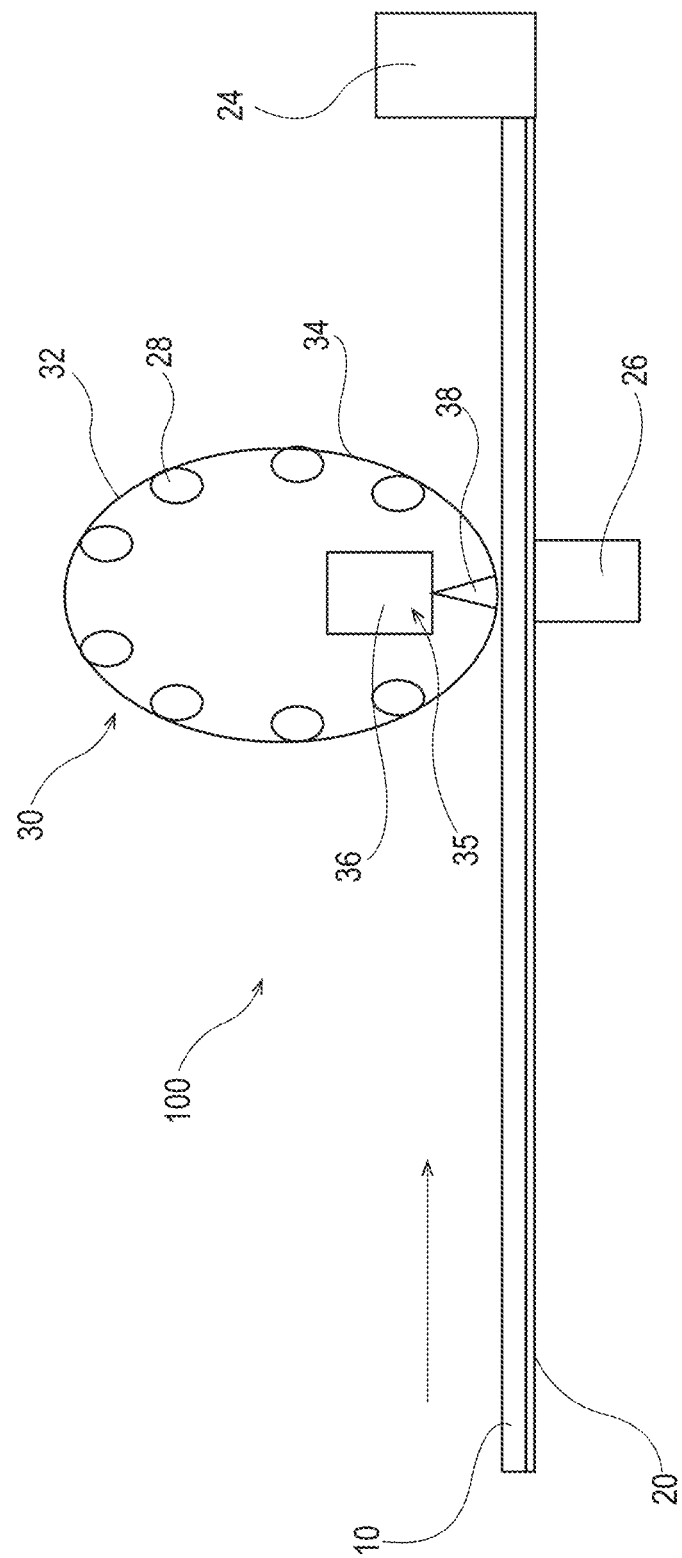
FIG. 1 is a schematic view of a fluid etching process.

The present invention relates to a method for etching an absorbent structure using fluid. The fluid may be at a high pressure. High pressure as used herein relates to a pressure of sufficient capacity to expel fluid with enough force to impact and modify portions of the absorbent structure. The absorbent structure may be a stratum such as, for example, a heterogeneous mass stratum. High pressure as used herein relates to a pressure of sufficient capacity to expel fluid with enough force to impact and modify portions the open cell foam within the heterogeneous mass stratum. The fluid may impact the enrobeable elements in the heterogeneous mass stratum. The heterogeneous mass stratum may be an absorbent core or a portion of an absorbent core.

As used herein, the term "absorbent core structure" refers to an absorbent core that is has two or more absorbent core layers. Each absorbent core layer is capable acquiring and transporting or retaining fluid.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, "complex liquids" are defined as fluids that are non-Newtonian, whose rheological properties are complex that change with shear and commonly shear thin. Such liquids commonly contain more than one phase (red blood cells plus vaginal mucous) that may phase separate on contact with topsheets and absorbent materials. In addition, complex liquids such as menstrual fluid may contain long chain proteins exhibiting stringy properties, high cohesive force within a droplet allowing for droplet elongation without breaking. Complex liquids may have solids (menstrual and runny feces).

The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent structure according to the present invention can be for example a sanitary napkin or a panty liner or an adult incontinence article or a baby diaper or a wound dressing. The absorbent structure of the present invention will be herein described in the context of a typical absorbent article, such as, for example, a sanitary napkin. Typically, such articles can comprise a liquid pervious topsheet, a backsheet and an absorbent core intermediate the topsheet and the backsheet.

As used herein, an "enrobeable element" refers to an element that may be enrobed by the foam. The enrobeable element may be, for example, a fiber, a group of fibers, a tuft, or a section of a film between two apertures. It is understood that other elements are contemplated by the present invention.

A "fiber" as used herein, refers to any material that can be part of a fibrous structure. Fibers can be natural or synthetic. Fibers can be absorbent or non-absorbent.

A "fibrous structure" as used herein, refers to materials which can be broken into one or more fibers. A fibrous structure can be absorbent or adsorbent. A fibrous structure can exhibit capillary action as well as porosity and permeability.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter. Thereafter, the meltblown fibers are carried by the high velocity gas stream and are deposited on a collecting surface, often while still tacky, to form a web of randomly dispersed meltblown fibers.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "non-round fibers" describes fibers having a non-round cross-section, and includes "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, spunlacing processes, needlepunching, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier or decitex, which is a unit of weight per length of fiber. The basis weight of laminate webs suitable for use in an article of the present invention can range from 5 gsm to 400 gsm, depending on the ultimate use of the web.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample size of at least 10 fibers) larger than 7 microns, and more particularly, between about 10 and 40 microns.

As used herein, a "strata" or "stratum" relates to one or more layers wherein the components within the stratum are intimately combined without the necessity of an adhesive, pressure bonds, heat welds, a combination of pressure and heat bonding, hydro-entangling, needlepunching, ultrasonic bonding, or similar methods of bonding known in the art such that individual components may not be wholly separated from the stratum without affecting the physical structure of the other components. The skilled artisan should understand that while separate bonding is unnecessary between the strata, bonding techniques could be employed to provide additional integrity depending on the intended use.

As used herein, a "tuft" or chad relates to discrete integral extensions of the fibers of a nonwoven web. Each tuft can comprise a plurality of looped, aligned fibers extending outwardly from the surface of the web. In another embodiment each tuft can comprise a plurality of non-looped fibers that extend outwardly from the surface of the web. In another embodiment, each tuft can comprise a plurality of fibers which are integral extensions of the fibers of two or more integrated nonwoven webs.

While particular embodiments of the present invention have been illustrated and described, it would be obvious to those skilled in the art that various other changes and modifications can be made without departing from the spirit and scope of the invention.

GENERAL SUMMARY

A method of etching an absorbent structure is disclosed. The absorbent structure may comprise a first layer and a second layer. The first layer may be a fibrous layer. The second layer may be a foam layer.

The fibrous web may be a heterogeneous mass comprising a fibrous web and one or more pieces of open cell foam intermixed within the fibrous web and/or enrobing one or more fibers within the fibrous web.

The fibrous web may be the upper layer of an absorbent core. The absorbent core may be a two layer system wherein the upper layer is heterogeneous mass layer comprising one or more enrobeable elements and one or more discrete open-cell foam pieces. The upper layer heterogeneous mass layer may be a stratum as defined above. The lower layer may be an absorbent layer that comprises superabsorbent polymer. The absorbent core structure may comprise additional layers below the absorbent layer that comprises super-absorbent polymer.

The absorbent article or the absorbent core structure in the absorbent article may comprise a heterogeneous mass layer as those described in U.S. patent application No. 61/988,565, filed May 5, 2014; U.S. patent application No. 62/115,921, filed Feb. 13, 2015; or U.S. patent application No. 62/018,212. The heterogeneous mass layer has a depth, a width, and a height.

The absorbent core structure may comprise a substrate and superabsorbent polymer layer as those described in U.S. Pat. No. 8,124,827 filed on Dec. 2, 2008 (Tamburro); U.S. application Ser. No. 12/718,244 published on Sep. 9, 2010; U.S. application Ser. No. 12/754,935 published on Oct. 14, 2010; or U.S. Pat. No. 8,674,169 issued on Mar. 18, 2014.

The one or more discrete portions of foam pieces enrobe the enrobeable elements. The discrete portions of foam pieces are open-celled foam. In an embodiment, the foam is a High Internal Phase Emulsion (HIPE) foam. In an embodiment, one continuous piece of open cell foam may enrobe multiple enrobeable elements, such as, for example, the fibers that make up the upper layer of a nonwoven web.

In the following description of the invention, the surface of the article, or of each component thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

The heterogeneous mass layer contains one or more discrete open-cell foam pieces foams that are integrated into the heterogeneous mass comprising one or more enrobeable elements integrated into the one or more open-cell foams such that the two may be intertwined.

The open-cell foam pieces may comprise between 1% of the heterogeneous mass by volume to 99% of the heterogeneous mass by volume, such as, for example, 5% by volume, 10% by volume, 15% by volume, 20% by volume, 25% by volume, 30% by volume, 35% by volume, 40% by volume, 45% by volume, 50% by volume, 55% by volume, 60% by volume, 65% by volume, 70% by volume, 75% by volume, 80% by volume, 85% by volume, 90% by volume, or 95% by volume.

The heterogeneous mass layer may have void space found between the enrobeable elements (e.g. fibers), between the enrobeable elements and the enrobed enrobeable elements (e.g. fibers enrobed by open cell foam), and between enrobed enrobeable elements. The void space may contain gas. The void space may represent between 1% and 95% of the total volume for a fixed amount of volume of the heterogeneous mass, such as, for example, 5%, 10%, 15%, 20%, 25%, 30%, 35%, 40%, 45%, 50%, 55%, 60%, 65%, 70%, 75%, 80%, 85%, 90% of the total volume for a fixed amount of volume of the heterogeneous mass.

The combination of open-cell foam pieces and void space within the heterogeneous mass may exhibit an absorbency of between 10 g/g to 200 g/g of the heterogeneous mass, such as for example, 40 g/g, 60 g/g, 80 g/g, 100 g/g, 120 g/g, 140 g/g 160 g/g 180 g/g or 190 g/g of the heterogeneous mass. Absorbency may be quantified according to the EDANA Nonwoven Absorption method 10.4-02.

The open-cell foam pieces are discrete foam pieces intertwined within and throughout a heterogeneous mass such that the open-cell foam enrobes one or more of the enrobeable elements such as, for example, fibers within the mass. The open-cell foam may be polymerized around the enrobeable elements.

In an embodiment, a discrete open-cell foam piece may enrobe more than one enrobeable element. The enrobeable elements may be enrobed together as a bunch. Alternatively, more than one enrobeable element may be enrobed by the discrete open-cell foam piece without contacting another enrobeable element.

In an embodiment, the open-cell foam pieces may enrobe an enrobeable element such that the enrobeable element is enrobed along the enrobeable elements axis for between 5% and 95% of the length along the enrobeable element's axis. For example, a single fiber may be enrobed along the length of the fiber for a distance greater than 50% of the entire length of the fiber. In an embodiment, an enrobeable element may have between 5% and 100% of its surface area enrobed by one or more open-cell foam pieces.

In an embodiment, two or more open-cell foam pieces may enrobe the same enrobeable element such that the enrobeable element is enrobed along the enrobeable elements axis for between 5% and 100% of the length along the enrobeable element's axis.

The open-cell foam pieces enrobe the enrobeable elements such that a layer surrounds the enrobeable element at a given cross section. The layer surrounding the enrobeable element at a given cross section may be between 0.01 mm to 100 mm such as, for example, 0.1 mm, 0.2 mm, 0.3 mm, 0.4 mm, 0.5 mm, 0.6 mm, 0.7 mm, 0.8 mm, 0.9 mm, 1.0 mm, 1.2 mm, 1.4 mm, 1.6 mm, 1.8 mm, 2.0 mm, 2.2 mm, 2.4 mm, 2.6 mm, 2.8 mm, or 3 mm. The layer may not be equivalent in dimension at all points along the cross section of the enrobeable element. For example, in an embodiment, an enrobeable element may be enrobed by 0.5 mm at one point along the cross section and by 1.0 mm at a different point along the same cross section.

The open-cell foam pieces are considered discrete in that they are not continuous throughout the entire heterogeneous mass layer. Not continuous throughout the entire heterogeneous mass layer represents that at any given point in the heterogeneous mass layer, the open-cell absorbent foam is not continuous in at least one of the cross sections of a longitudinal, a vertical, and a lateral plane of the heterogeneous mass layer. In a non-limiting embodiment, the absorbent foam is not continuous in the lateral and the vertical planes of the cross section for a given point in the heterogeneous mass layer. In a non-limiting embodiment, the absorbent foam is not continuous in the longitudinal and the vertical planes of the cross section for a given point in the heterogeneous mass layer. In a non-limiting embodiment, the absorbent foam is not continuous in the longitudinal and the lateral planes of the cross section for a given point in the heterogeneous mass layer.

In an embodiment wherein the open-cell foam is not continuous in at least one of the cross sections of the longitudinal, the vertical, and the lateral plane of the heterogeneous mass, one or both of either the enrobeable elements or the open-cell foam pieces may be bi-continuous throughout the heterogeneous mass.

The open-cell foam pieces may be located at any point in the heterogeneous mass. In a non-limiting embodiment, a foam piece may be surrounded by the elements that make up the enrobeable elements. In a non-limiting embodiment a foam piece may be located on the outer perimeter of the heterogeneous mass such that only a portion of the foam piece is entangled with the elements of the heterogeneous mass.

In a non-limiting embodiment, the open-cell foam pieces may expand upon being contacted by a fluid to form a channel of discrete open-cell foam pieces. The open-cell foam pieces may or may not be in contact prior to being expanded by a fluid.

An open-celled foam may be integrated onto the enrobeable elements prior to being polymerized. In a non-limiting embodiment the open-cell foam pieces may be partially polymerized prior to being impregnated into or onto the enrobeable elements such that they become intertwined. After being impregnated into or onto the enrobeable elements, the open-celled foam in either a liquid or solid state are polymerized to form one or more open-cell foam pieces.

The open cell foam pieces may be impregnated prior to polymerization into or onto two or more different enrobeable elements that are combined to create a heterogeneous mixture of enrobeable elements. The two or more different enrobeable elements may be intertwined such that one enrobeable element may be surrounded by multiples of the second enrobeable element, such as, for example by using more than one type of fiber in a mixture of fibers or by coating one or more fibers with surfactant. The two or more different enrobeable elements may be layered within the heterogeneous mass along any of the vertical, longitudinal, and/or lateral planes such that the enrobeable elements are profiled within the heterogeneous mass for an enrobeable element inherent property or physical property, such as, for example, hydrophobicity, fiber diameter, fiber or composition. It is understood that any inherent property or physical property of the enrobeable elements listed is contemplated herein.

The open-celled foam may be polymerized using any known method including, for example, heat, UV, and infrared. Following the polymerization of a water in oil open-cell foam emulsion, the resulting open-cell foam is saturated with aqueous phase that needs to be removed to obtain a substantially dry open-cell foam. Removal of the saturated aqueous phase or dewatering may occur using nip rollers, and vacuum. Utilizing a nip roller may also reduce the thickness of the heterogeneous mass such that the heterogeneous mass will remain thin until the open-cell foam pieces entwined in the heterogeneous mass are exposed to fluid.

Dependent upon the desired foam density, polymer composition, specific surface area, or pore size (also referred to as cell size), the open-celled foam may be made with different chemical composition, physical properties, or both. For instance, dependent upon the chemical composition, an open-celled foam may have a density of 0.0010 g/cc to about 0.25 g/cc. Preferred 0.04 g/cc.

Open-cell foam pore sizes may range in average diameter of from 1 to 800 μm, such as, for example, between 50 and 700 μm, between 100 and 600 μm, between 200 and 500 μm, between 300 and 400 μm.

In some embodiments, the foam pieces have a relatively uniform cell size. For example, the average cell size on one major surface may be about the same or vary by no greater than 10% as compared to the opposing major surface. In other embodiments, the average cell size of one major surface of the foam may differ from the opposing surface. For example, in the foaming of a thermosetting material it is not uncommon for a portion of the cells at the bottom of the cell structure to collapse resulting in a lower average cell size on one surface.

The foams produced from the present invention are relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "open-celled" if at least about 80% of the cells in the foam that are at least 1 μm in average diameter size are in fluid communication with at least one adjoining cell.

In addition to being open-celled, in certain embodiments foams are sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

In certain embodiments, for example when used in certain absorbent articles, an open-cell foam may be flexible and exhibit an appropriate glass transition temperature (Tg). The Tg represents the midpoint of the transition between the glassy and rubbery states of the polymer.

In certain embodiments, the Tg of this region will be less than about 200° C. for foams used at about ambient temperature conditions, in certain other embodiments less than about 90° C. The Tg may be less than 50° C.

The open-cell foam pieces may be distributed in any suitable manner throughout the heterogeneous mass. In an embodiment, the open-cell foam pieces may be profiled along the vertical axis such that smaller pieces are located above larger pieces. Alternatively, the pieces may be profiled such that smaller pieces are below larger pieces. In another embodiment, the open-cell pieces may be profiled along a vertical axis such that they alternate in size along the axis.

In an embodiment the open-cell foam pieces may be profiled along any one of the longitudinal, lateral, or vertical axis based on one or more characteristics of the open-cell foam pieces. Characteristics by which the open-cell foam pieces may be profiled within the heterogeneous mass may include, for example, absorbency, density, cell size, and combinations thereof.

In an embodiment, the open-cell foam pieces may be profiled along any one of the longitudinal, lateral, or vertical axis based on the composition of the open-cell foam. The open-cell foam pieces may have one composition exhibiting desirable characteristics in the front of the heterogeneous mass and a different composition in the back of the heterogeneous mass designed to exhibit different characteristics.

The profiling of the open-cell foam pieces may be either symmetric or asymmetric about any of the prior mentioned axes or orientations.

The open-cell foam pieces may be distributed along the longitudinal and lateral axis of the heterogeneous mass in any suitable form. In an embodiment, the open-cell foam pieces may be distributed in a manner that forms a design or shape when viewed from a top planar view. The open-cell foam pieces may be distributed in a manner that forms stripes, ellipticals, squares, or any other known shape or pattern.

In an embodiment, different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

In an embodiment, the open-celled foam is a thermoset polymeric foam made from the polymerization of a High Internal Phase Emulsion (HIPE), also referred to as a polyHIPE. To form a HIPE, an aqueous phase and an oil phase are combined in a ratio between about 8:1 and 140:1. In certain embodiments, the aqueous phase to oil phase ratio is between about 10:1 and about 75:1, and in certain other embodiments the aqueous phase to oil phase ratio is between about 13:1 and about 65:1. This is termed the "water-to-oil" or W:O ratio and can be used to determine the density of the resulting polyHIPE foam. As discussed, the oil phase may contain one or more of monomers, co-monomers, photo-initiators, cross-linkers, and emulsifiers, as well as optional components. The water phase will contain water and in certain embodiments one or more components such as electrolyte, initiator, or optional components.

The open-cell foam can be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, and in certain embodiments, after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE can then be withdrawn or pumped from the mixing zone. One method for forming HIPEs using a continuous process is described in U.S. Pat. No. 5,149,720 (DesMarais et al), issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

The emulsion can be withdrawn or pumped from the mixing zone and impregnated into or onto a mass prior to being fully polymerized. Once fully polymerized, the foam pieces and the elements are intertwined such that discrete foam pieces are bisected by the elements comprising the mass and such that parts of discrete foam pieces enrobe portions of one or more of the elements comprising the heterogeneous mass.

The emulsion may be fluid etched upon reaching a gel point. The emulsion may be fluid etched once it has polymerized into a foam. The emulsion may be fluid etched at any point between gel point polymerization and 100% polymerization. As used herein gel point relates to the point at which the emulsion has shifted from a liquid phase to a more solid like phase.

The fluid etching system may be located at any location in the process after the gel point such as, for example, prior to exiting the curing oven, after the curing oven, prior to dewatering the foam, after dewatering the foam, between a first curing oven and a second curing oven. In an embodiment, the first curing oven may allow for etching of the material within the oven prior to exposing the material to additional heat in the oven. The fluid etching may occur when the foam is fully expanded or after the foam has been compressed due to dewatering.

The fluid etching system may have one or more etching jets, such as, for example, less than 100 jets, between 1 and 100 jets, between 1 and 50 jets, between 5 and 25 jets, and between 10 and 20 jets.

In an embodiment, the fluid etching tool comprises of a line of fluid expelling jets that run along the transverse length of the core. The absorbent core passes under the etching jets. The etching jets are controlled to expel fluid at set velocities and pressures. The velocities may be varied as the absorbent core passes under the web. The etching jets may be programmed to create a pattern on the absorbent core. For example, as a portion of the absorbent core passes under the etching jets, different jets may expel no fluid while other etching jets expel fluid at different velocities. Alternatively, the etching jets may move as the core passes under the fluid etching jets. For example, one or more jets may be connected such that the jets move back and forth along the width of the core to create a wave pattern. Additionally, one or more jets may be located to a single wheel that spins as the core moves under the fluid etching jets. Additionally, one or more fluid etching jets may be on an arm capable of etching out any desirable pattern. As the absorbent core continues to pass under the etching jets, the etching jets may vary in velocity and amount of fluid being expelled to create a predetermined pattern onto the absorbent core. Additionally, the spacing between etching jets may be variable to create different patterns.

In a further embodiment, the fluid etching jets can be contained in a fluid etching head that runs along the transverse length of the core. The number of fluid etching jets contained within a fluid etching head can vary depending on the width of the core passing underneath the fluid etching head such that the number of jets per inch are capable of delivering the desired pattern onto the absorbent core. For example, if the width is one foot and the desire is to have five jets per inch, then the fluid etching head may contain 60 fluid etching jets.

In an embodiment, the fluid etching system comprises of a line of fluid expelling jets that run along the transverse length of the core and the stencil comprising one or more patterns. The stencil, when utilized, may be located between the etching jets and the absorbent core when the absorbent core passes under the etching jets.

The fluid etching may be done with or without a stencil. Additionally, the fluid etching may be done in a two stage process wherein the first or second stage does not utilize a stencil and the other stage uses a stencil. The stencil may be in the form of a fixed stencil, a drum comprising a stencil, a cylinder having a stencil, a belt with apertures serving as the stencil, or a combination thereof. The stencil may have one continuous pattern, may have a walking pattern that is not set to a product pitch length, or may have a pattern that is set to a product pitch. The stencil may have more than one pattern wherein each pattern represents one of a walking pattern that is not equivalent to a product pitch or a pattern that is equivalent to a product pitch. The stencil pattern may be made of apertures in a repeating pattern. The stencil apertures may be in a random pattern. The stencil pattern may create, without limitation, a simple repeating pattern, non-repeating patterns, one or more words in any form of script used by any language, such as, for example, Mandarin characters, the Roman alphabet, the Greek alphabet, Japanese characters and in any font inclusive of cursive, or any other pattern imaginable inclusive of flowers, hearts, animals, images of abstract items. It is understood that the stencil pattern may be of any pattern that may be made using a stencil. The pattern may be different for along the width of the material being etched. For example, a first pattern may be located along 50% of the width of the material being etched and second pattern may be located along the other 50% of the width of the material being etched.

The stencils may repeat along the belt or may not. The stencil may be continuously repeating on a drum, belt, or any other rotating form. The drum or belt may have all unique stencils or repeat the same stencil. The stencil may be interchanged to add different patterns. For example, in the context of a drum or belt, different aspects of the belt or drum may be removed while leaving others such that one may change the stencils. The belt may be continuous, with bearings on both sides, cantilevered, or having a seam.

The belt may comprise of any material capable of surviving the chosen conditions in the process. The belt may be made of metal, one or more polymers, or combinations thereof.

Examples of belts may include endless belts made of one or more metals, a resin, or combinations thereof; or sheet materials such as films that may be positioned on the belt and moving therewith.

The belt may be of any dimension or configuration provided that it is parallel to the heterogeneous mass stratum when under the fluid etching jet.

The stencil may be made of any material capable of surviving the chosen conditions in the process. The stencil may be made of metal, one or more polymers, or combinations thereof.

A rotating stencil in the form of a drum or belt may be driven by its own motor or may be driven by an idler roller. The stencil may contact the absorbent core prior at a given point and be driven by the absorbent core roller. Additionally, both the absorbent core belt and the stencil may be driven by their own independent motors.

The stencil is located between the etching jets and the absorbent core. The stencil allows for fluid exiting the etching jets to contact the material being etched. If the stencil is a hollow cylinder, then the cylinder pattern comprises of one or more apertures in the cylinder that allows fluid to pass through the cylinder. The apertures may be in the form of any visual pattern imaginable. Upon exiting the cylinder, the fluid allowed to pass through the stencil contacts the absorbent core thereby replicating the cylinder pattern onto the absorbent core. The cylinder may have one repeating pattern or a plurality of patterns. Each pattern may be equivalent to the length of one absorbent core in the machine direction.

The fluid etching process may utilize more than one stage wherein a first stage has a first set of one or more etching jets and a second stage has a second set of one or more etching jets. Each of the first stage and the second stage may or may not have a stencil. The two stage approach may be utilized to create both voids and fissures. For example, the voids may be created at the first stage having a first pattern while the fissures may be created at the second stage having a second pattern; the resultant etched material having a pattern that is visible from above and additionally a pattern along the vertical Z direction that may be exhibited in a cross section of the etched material. It is understood that more than two stations may be used and/or that a stage may contain more than one etching jet, more than one fluid, and more than one stencil.

The fluid may consist of at least 50% dihydrogen oxide, such as, for example, 60% dihydrogen oxide, 70% dihydrogen oxide, 80% dihydrogen oxide, 90% dihydrogen oxide, 100% dihydrogen oxide, such as, for example, between 80% and 100% dihydrogen oxide. The fluid may contain other items such as, for example, process modifiers, salts used in the process, surfactants, perfume, modifiers enabled to change the hydrophilic/hydrophobic balance of the stratum of heterogeneous layer, any additive to change the structure of the open cell foam, or combinations thereof. The fluid may contain a particulate such as, silica, metal particles, polymers, or combinations thereof. The fluid may contain one or more process modifiers capable of affecting the properties of the fibrous layer, such as, for example, adding citric acid to the fluid to further crosslink a nonwoven web. Additionally, the fluid may be used to modify the pH of the absorbent stratum.

The carrier belt carries the absorbent structure through the fluid etching process. The carrier belt can be any thickness or shape suitable. Further, the surface of the belt can be substantially smooth or may comprise depressions, protuberances, or combinations thereof. The pattern on the belt may be designed to work with the stencil pattern such that the two patterns are coordinated to create a predetermined pattern. The protuberances or depressions may be arranged in any formation or order to create the pattern in the carrier belt. The belt may comprise one or more materials suitable for the polymerization conditions (various properties such as heat resistance, weatherability, surface energy, abrasion resistance, recycling property, tensile strength and other mechanical strengths) and may comprise at least one material from the group including films, non-woven materials, woven materials, and combinations thereof. Examples of films include, fluorine resins such as polytetrafluoroethylene, tetrafluoroethylene-perfluoroalkylvinyl ether copolymers, tetrafluoroethylene-hexafluoropropylene copolymers, and tetrafluoroethylene-ethylene copolymers; silicone resins such as dimethyl polysiloxane and dimethylsiloxane-diphenyl siloxane copolymers; heat-resistant resins such as polyimides, polyphenylene sulfides, polysulfones, polyether sulfones, polyether imides, polyether ether ketones, and para type aramid resins; thermoplastic polyester resins such as polyethylene terephthalates, polybutylene terephthalates, polyethylene naphthalates, polybutylene naphthalates, and polycyclohexane terephthalates, thermoplastic polyester type elastomer resins such as block copolymers (polyether type) formed of PBT and polytetramethylene oxide glycol and block copolymers (polyester type) formed of PBT and polycaprolactone may be used. These materials may be used either singly or in mixed form of two or more materials. Further, the belt may be a laminate comprising two or more different materials or two or more materials of the same composition, but which differ in one or more physical characteristics, such as quality or thickness.

The fluid etching system may be designed to add between 0.2 to 50 kilowatt hour/kilogram to the absorbent structure, such as for example, between 0.5 to 40 kilowatt hour/kilogram, between 1 to 30 kilowatt hour/kilogram, or between 5 to 20 kilowatt hour/kilogram. One of ordinary skill in the art would understand that the amount of energy inserted into an absorbent structure such as, for example, an absorbent stratum, by the etching system is based on the jet diameters of the individual jets and the pressure at which the jets are ran. As such, more than one configuration may be used to achieve the desired energy insertion level.

The fluid etching system may run at a pressure between 20 and 400 bar, such as, for example, between 20 and 350 bar, 30 and 320 bar, 40 and 300 bar, 50 and 250 bar, 60 and 200 bar, 70 and 150 bar, 80 and 100 bar. The fluid etching system may run at a pressure between 20 and 100 bar.

The fluid jet diameter may be between 20-400 microns, such as for example, between 30 and 300 microns, between 40 and 250 microns, between 50 and 200 microns, between 75 and 150 microns, and between 100 and 125 microns. The fluid jet diameter may be variable throughout or fixed.

The etching system may input energy into a heterogeneous mass layer or into an absorbent core or into an absorbent stratum. The total amount of energy input into a system may be based upon the fluid pressure and the number of etching jets. The energy may be calculated according to the following equation:

$$\text{Specific Energy} = 2.622 * \frac{10^3 \left( \left( Cd_1^2 P_g^{\frac{3}{2}} \right) * N * \text{Passes} \right)}{WS} \left( \frac{kJ}{kg} \right)$$

Where:
C=coefficient of discharge, dimensionless
$d_1$=inlet diameter, mm
$P_g$=gauge pressure, bar
N=number of jets per inch of manifold
Passes=number of passes acted on etched layer
W=basis weight, g/m$^2$
S=line speed, m/min The fluid etch system may be designed to remove or displace foam from a heterogeneous mass layer. The fluid etching system may be designed to create a three dimensional pattern within the foam layer having one of fissures alone, voids alone, or a combination of both fissures and voids.

Without being bound by theory, removal, displacement, or destruction of the foam, during the etching process can be explained partially by cavitation. When a liquid jet (for this example, a cross-section of a column of liquid) reaches or enters the foam, the liquid encounters a certain number of cells within the foam. As the jet liquid enters these cells of the foam it then moves between adjacent and lower cells through the smaller, intercellular opening or windows. The initial velocity of the jet may thereby be subdivided between the number of cells that is covered by the cross-sectional area of the liquid jet, and, then be further subdivided by the number of windows within these affected cells. On each side of these windows is an open cell of a larger size than the window the liquid is passing through to get to it. This sudden change in opening size, or orifice, may result in a sudden change in fluid pressure. This sudden change in fluid pressure, from high to low, may result in cavitation.

For example, if the open-celled foam has cells of 50 micron diameter, it may have windows of 1.7 micron diameter and there may be up to 20 windows in that cell that lead to the next cell of 50 micron diameter. By knowing the fluid jet's velocity and cross-sectional diameter, the number of cells impinged can be calculated, and therefore, the number of windows to flow though. For this instance, a 2.8×10−8 m$^3$/sec fluid jet's volumetric flowrate can impinge 565 windows of 1.7 micron diameter such that the individual window velocity is 22 m/sec. If the fluid is dihydrogen oxide, then one can enter these values into the Cavitation Equation (K). Since the foam is open-celled and at room temperature and pressure, the static pressure just downstream of the window or orifice is 101325 Pa. The density of dihydrogen oxide is 1000 kg/m$^3$ and its vapor pressure is 3167 Pa. The mean velocity through the window or orifice hole is 22 m/sec. The resultant Cavitation Number (K) is 0.4 and those skilled in the art know that this indicates cavitation since K is less than 1. If K is greater than 1, then cavitation isn't occurring. As the fluid passes through more and more cells and windows, cavitation will cease once the velocity gets low enough to bring the Cavitation Number above 1. Therefore, if one knows the cell size, number of cells per area, the window size, and the number of windows in the cells, one skilled in the art can design the water jet such that it imparts just the right volumetric flow rate, over a desired cross-sectional area, to impart just the right level of cavitation so that the depth and extent of removal can be obtained.

$$K = \frac{P_{dl} - P_v}{\frac{1}{2} * \rho * v_0^2}$$

Wherein K is the cavitation number; $P_{dl}$ is the static pressure just at downstream of the orifice (Pa); $P_v$ is the vapor pressure of fluid (Pa); ρ is the density of fluid (kg/m$^3$); and $v_0$ is the mean velocity through the orifice hole (m/s).

After polymerization, the absorbent structure may go through a fluid etching process. The fluid etching process utilizes one or more fluids to modify portions of the absorbent structure by impacting the open celled foam and/or the enrobeable elements. The fluid etching process includes exposing at least a portion of the absorbent structure to one or more jets capable of expelling fluid at a desired velocity driven by the pressure in the fluid expelling jets. The absorbent structure may be an absorbent stratum, an absorbent core, or a portion of an absorbent core. The absorbent structure, may or may not comprise the topsheet or a secondary topsheet.

The fluid etching process may be coordinated with the carrier belt. The etching jets may oscillate to create a wave pattern on the absorbent core.

In an embodiment, the polymerized absorbent core is exposed to one or more etching jets that are attached to a carrier system. The carrier system is allowed to move over the web thereby allowing the individual jets to cover the entire top surface area of the absorbent core. The jets may be arranged in any geometric order such as in a square pattern, in a circular pattern, in a line pattern. The carrier system may move over the absorbent core within a predetermined space. The carrier system may have an arm with a pivot that moves the one or more etching jets over the predetermined space. The space may be the entire area of the absorbent core or a partial area of the absorbent core.

Applicants have surprisingly found that one may create a pattern of different depths within an absorbent foam core by using one or more fluid expelling jets. The fluid etching process may create fissures that do not cross through the absorbent foam or may create voids that may cross through the absorbent foam. When fissures are created, the fissures may be seen from the surface that was fluid etched and may not be seen from the surface that was not etched. The fissures may penetrate between 1% and 99% of the foam absorbent layer, such as, for example, between 5% and 90%, between 10% and 80%, between 15% and 70%, between 20% and 60%, between 25% and 50%. When the fluid etching process creates voids, the voids may be seen from the first surface and from the second surface.

Without being bound by theory, it has been found that the addition of fissures and voids to the absorbent structure serves to increase the surface area within the absorbent structure and allows for the fissures and voids to create points of bending in one of the machine direction, cross direction, or along the vertical plane, while allowing the absorbent structure having the fissures and voids to maintain a structural integrity substantially equal to the same absorbent structure without the fissures and voids.

Voids may comprise of different density portions of foam within the void when compared to the rest of the foam layer. The different density portions of foam may exhibit a higher density than the areas adjacent to the void within the layer.

As shown in FIGS. 4, 5 and 8-13 below, the velocity of the fluid and the duration of time the absorbent core is exposed to the fluid at a given velocity impacts the amount of energy placed into the absorbent core for a given area of the core thereby impacting the absorbent material in the core. As such, one may vary the depth of impact to the absorbent core at a given point along the vertical direction based upon the amount of energy input into the absorbent core. As a result, the absorbent foam is selectively fractured in comparison to the adjacent foam that is undisturbed. Fluid etching jets are utilized in the present invention to modify as-made absorbent materials into absorbent materials having relatively higher permeability and increased surface area without a significant corresponding decrease in capillary pressure and without a significant corresponding decrease in structural integrity for the absorbent structure. Additionally, the use of fluid etching surprisingly allows one to modify the open cell foam at the micro level. For example, using fluid etching, one may modify the foam between two fibers without impacting the fibers. Depending on the setting used during fluid etching, it has been found that the process described above allows for the creation of shapes that cannot be accomplished by using a mechanical removal/displacement process. Essentially, using fluid etching allows for one to modify one or more pieces of absorbent foam at a micro level versus a macro level.

It has also been surprisingly found that by modifying or removing one or more open cell foam pieces within a heterogeneous mass stratum, one may modify fluid handling properties, mechanical properties including but not limited to stiffness without breaking the enrobeable element. Additionally, when the enrobeable elements include a nonwoven web, one may fluid etch the heterogeneous mass without breaking or significantly displacing fibers within the nonwoven web. As shown in FIGS. 2-6, the fluid etching process maintains the fibrous web substantially planar while modifying the layer under or over the fibrous web. It has been surprisingly found that by using the method described, one may modify the open cell foam at the micro level. For example, using fluid etching, one may modify the foam between two fibers without impacting the fibers.

Furthermore, the modified absorbent layers exhibit improved fluid acquisition properties and improved structural properties.

Additionally, the ability to fluid etch the foam within the heterogeneous mass stratum allows for the creation of absorbent zones. The zones may be created along the longitudinal, latitudinal, or vertical planes. The fluid etching process may be used to create deeper perforation zones within the open cell foam versus other zones by increasing and reducing the fluid pressure as appropriate to create the desired zones.

FIG. 1 shows a schematic of the method 100 disclosed in the specification. As shown in the figure the absorbent structure 10 is placed on a carrier belt 20. The carrier belt 20 carries the absorbent structure 10 under a fluid etching system 30. The fluid etching system 30 may include a stencil 32 which may be a pattern belt 34 ran by rollers 28, and one or more fluid jets 36. When the absorbent structure 10 passes under the fluid etching system 30, the fluid 38 contacts the stencil 32 and impacts the absorbent structure 10 where open spaces exist in the stencil 32. Dependent upon the settings of the process, the fluid 38 may either form fissures 42 (not shown) in the absorbent structure 10 or voids 44 (not shown) in the absorbent structure 10.

Figure 7:
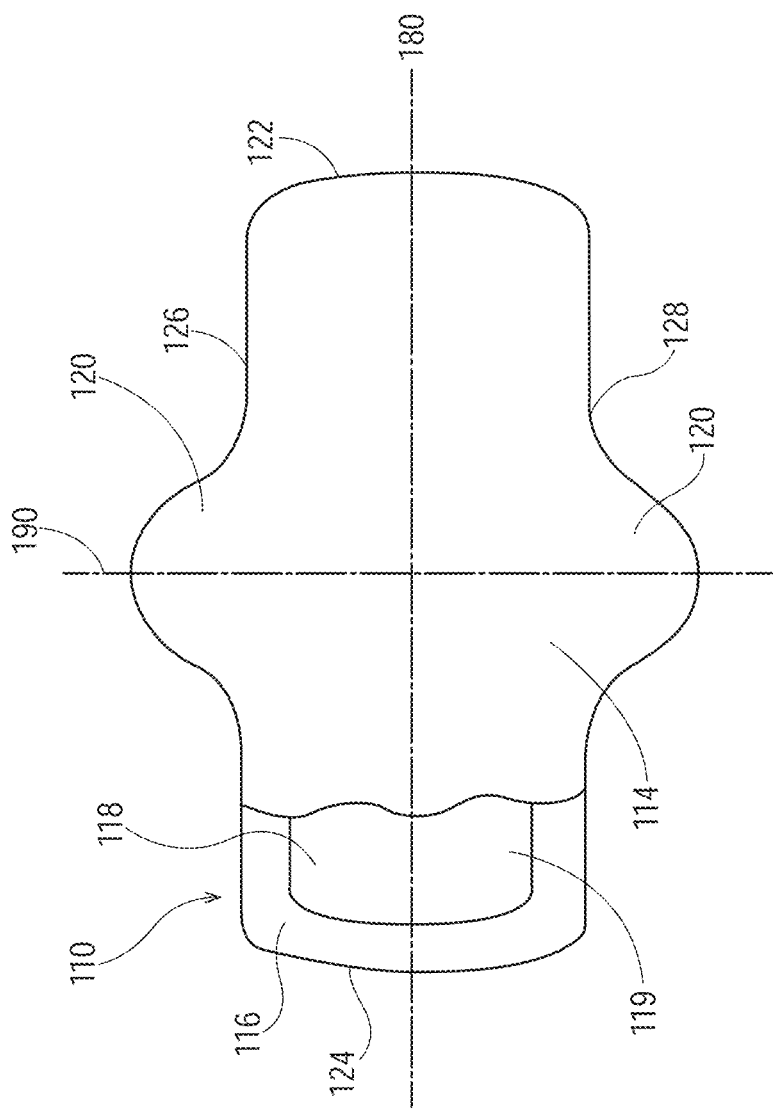
FIG. 7 is a plan view of an absorbent article.

As is to be appreciated, the patterned absorbent structure produced by the process of FIG. 1 may be used in the manufacturing of a variety of absorbent articles, such as the sanitary napkin 110 of FIG. 7, as well as a variety of other absorbent articles, including diapers, training pants, adult incontinence undergarments, and the like.

During the etching process, the absorbent structure 10 is passed by the jet head 35 that comprises a plurality of injectors that are positioned to generally form a water curtain (for simplicity of illustration, only one injector 36 is illustrated in FIG. 1). A water jet 38 is directed into the stratum of heterogeneous mass 12 at high pressures, such as between 150 to 400 bar. As is to be appreciated, while not illustrated, one or more rows of injectors 36 may be used, which may be positioned on one or both sides of the stratum of absorbent structure 10.

The absorbent structure 10 may be supported by any suitable support system or carrier belt 20, such as a moving wire screen or on a rotating porous drum, for example. While not illustrated, it is to be appreciated that fluid etching systems may expose the stratum of heterogeneous mass 12 to a series of jet heads (not shown) along the machine direction, with each delivering water jets at different pressures. The particular number of jet heads utilized may be based on, for example, desired basis weight, amount of etching, characteristics of the web, and so forth. As the fluid from an etching jet 36 penetrates the web, a vacuum 26 having suction slots positioned proximate beneath the stratum of heterogeneous mass 12 collects the water so that it may be filtered and returned to the etching jet 36 for subsequent injection. The fluid 38 delivered by the etching jet 36 exhausts most of its kinetic energy primarily in etching the absorbent structure second layer 16 within a stratum of heterogeneous mass 12.

Any fluid used for etching may be collected by any means known in the art such as, for example, a vacuum box (shown in FIG. 1), gravity, nip rollers, or a combination thereof. The collected fluid may be recycled and reused in the system. Additionally, the collected fluid may be treated to remove any undesired carryover and to prevent microbial growth.

Once a stratum of heterogeneous mass 12 has been fluid etched, the fluid etched stratum of heterogeneous mass 12 is then passed through a dewatering device where excess water is removed. In the process illustrated in FIG. 1, the dewatering device is a drying unit 24. The drying unit 24 may be any suitable drying system, such as a multi-segment multi-level bed dryer, a vacuum system, and/or an air drum dryer, for example. The drying unit 24, or other dewatering device, serves to substantially dry the fluid etched stratum of heterogeneous mass 12 before subsequent heat treatment. The term "substantially dry" is used herein to mean that the fluid etched stratum of heterogeneous mass has a liquid content, typically water or other solution content, less than about 10%, less than about 5%, or less than about 3%, by weight. Once the fluid etched stratum of heterogeneous mass is substantially dry, the fluid etched stratum of heterogeneous mass may be heated to an elevated temperature. By heating the fluid etched stratum of heterogeneous mass to a particular temperature, or temperature range, the flexural rigidity of the fluid etched stratum of heterogeneous mass may be increased (i.e., stiffened). Additionally one may heat the fluid inserted into the stratum. Stiffening the fluid etched stratum of heterogeneous mass results in a number of desired results. For example, the increase of stiffness of the fluid etched stratum of heterogeneous mass allows the structure to tolerate the subsequent manufacturing processes. Additionally, when the fluid etched stratum of heterogeneous mass 30 is subsequently incorporated into an absorbent article, such as sanitary napkin 10, for example, cross machine direction (CD) bunching is reduced, leading to less leakage and more comfort for a wearer. Additionally, one may selectively heat the stratum itself to change properties of the fibers for selective portions of the absorbent stratum. Any means known in the art to selectively target fibers may be used such as, for example, infrared or microwaves.

FIG. 1 shows a schematic of the method 100 disclosed in the specification. As shown in the figure the absorbent structure 10 is placed on a carrier belt 20. The carrier belt 20 carries the absorbent structure 10 under a fluid etching system 30. The fluid etching system 30 may include a stencil 32 which may be a pattern belt 34 ran by rollers 28, and one or more fluid jets 36. When the absorbent structure 10 passes under the fluid etching system 30, the fluid 38 passes through the stencil 32 and impacts the absorbent structure 10. Dependent upon the settings of the process, the fluid 38 may either form fissures 42 (not shown) in the absorbent structure 10 or voids 44 (not shown) in the absorbent structure 10.

Figure 2:
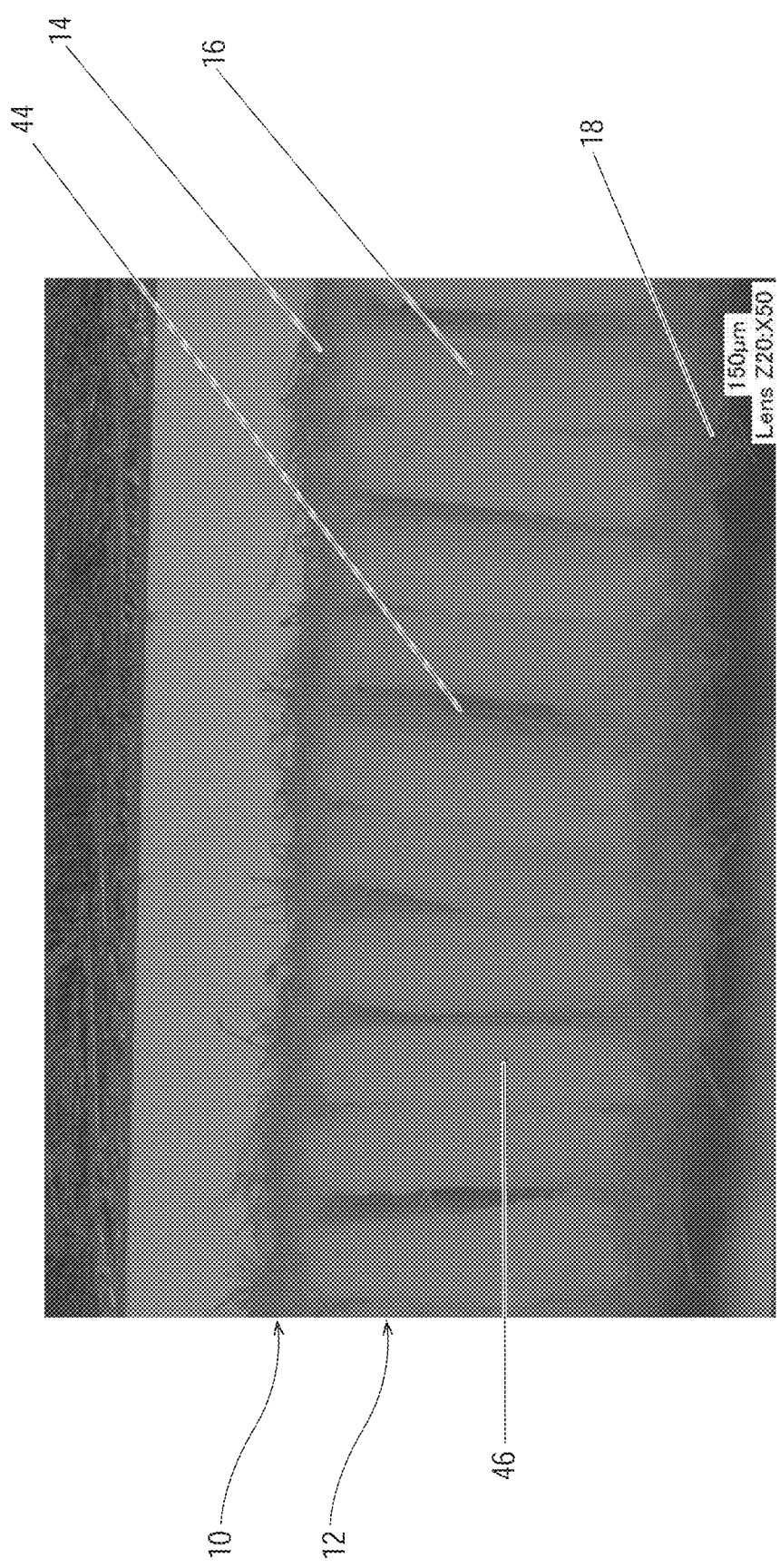
FIG. 2 is a cross-sectional view of an etched absorbent layer.

FIG. 2 represents a 50× magnification of a light microscopy image of a fluid etched absorbent structure 10, herein an absorbent stratum 12. As shown in the figure, the absorbent stratum 12 has three distinct layers, a first fibrous layer 14 having a first surface 13 and a second surface 15, a foam layer 16 having a first surface 17 and a second surface 19, and a second fibrous layer 18 having a first surface 21 and second surface 23. As shown in the figure, the fluid etching has penetrated through the foam layer 16 to create voids 44. Additionally, as shown in the figure, the first fibrous layer 14 above and the second fibrous layer 18 below the foam has remained unharmed and are substantially planar.

Figure 3:
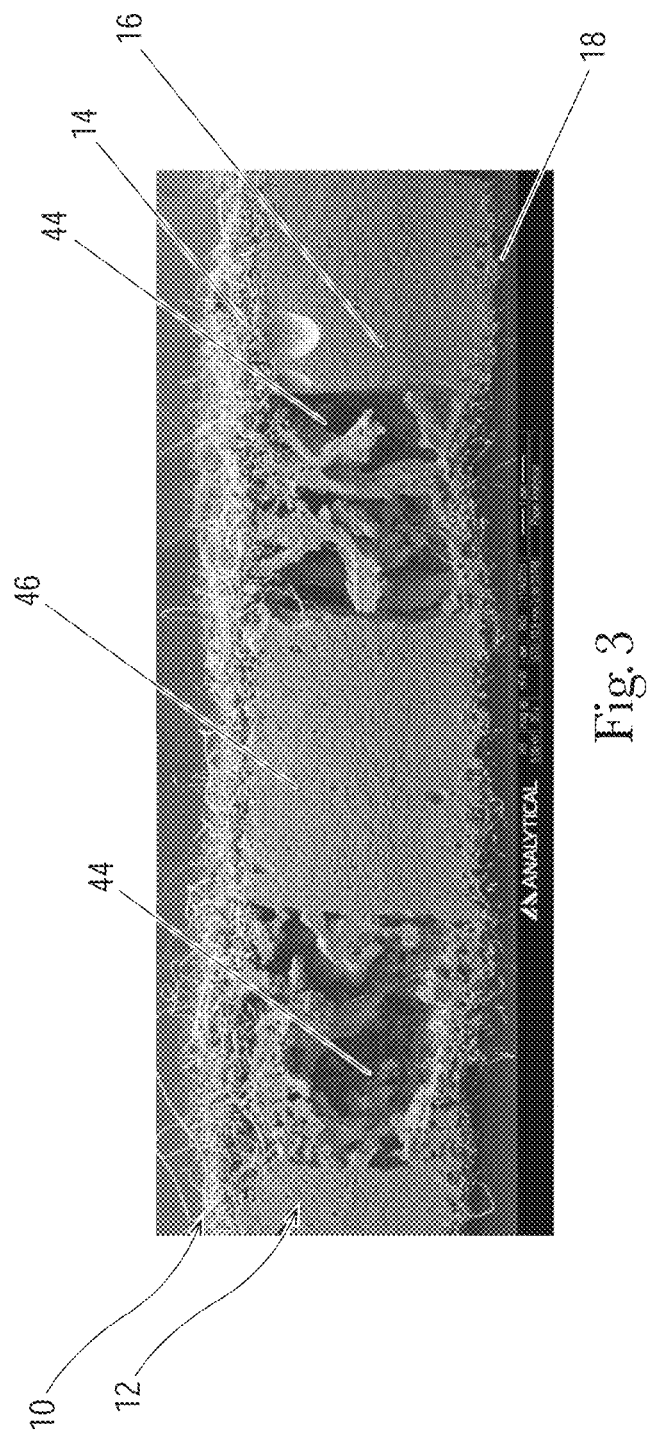
FIG. 3 is an SEM of a cross section of a fluid etched absorbent layer.

FIG. 3 is an SEM of a fluid etched heterogeneous stratum layer 12. As shown in the figure taken at a magnification of 35×, the fluid has penetrated through the first fibrous layer 14 and into the foam layer 16. As shown in the image, the use of the fluid etching allows one to leave unchanged sections 46 while creating voids 44. The layer exemplified in FIG. 3 was created using a larger hole stencil. The stencil allowed for an increased amount of fluid to penetrate the absorbent structure 10 during the residence time spent under the fluid jet. As shown in the figure, foam has been removed from the desired areas without damaging the fibrous network above and below the foam which are substantially planar.

Figure 4:
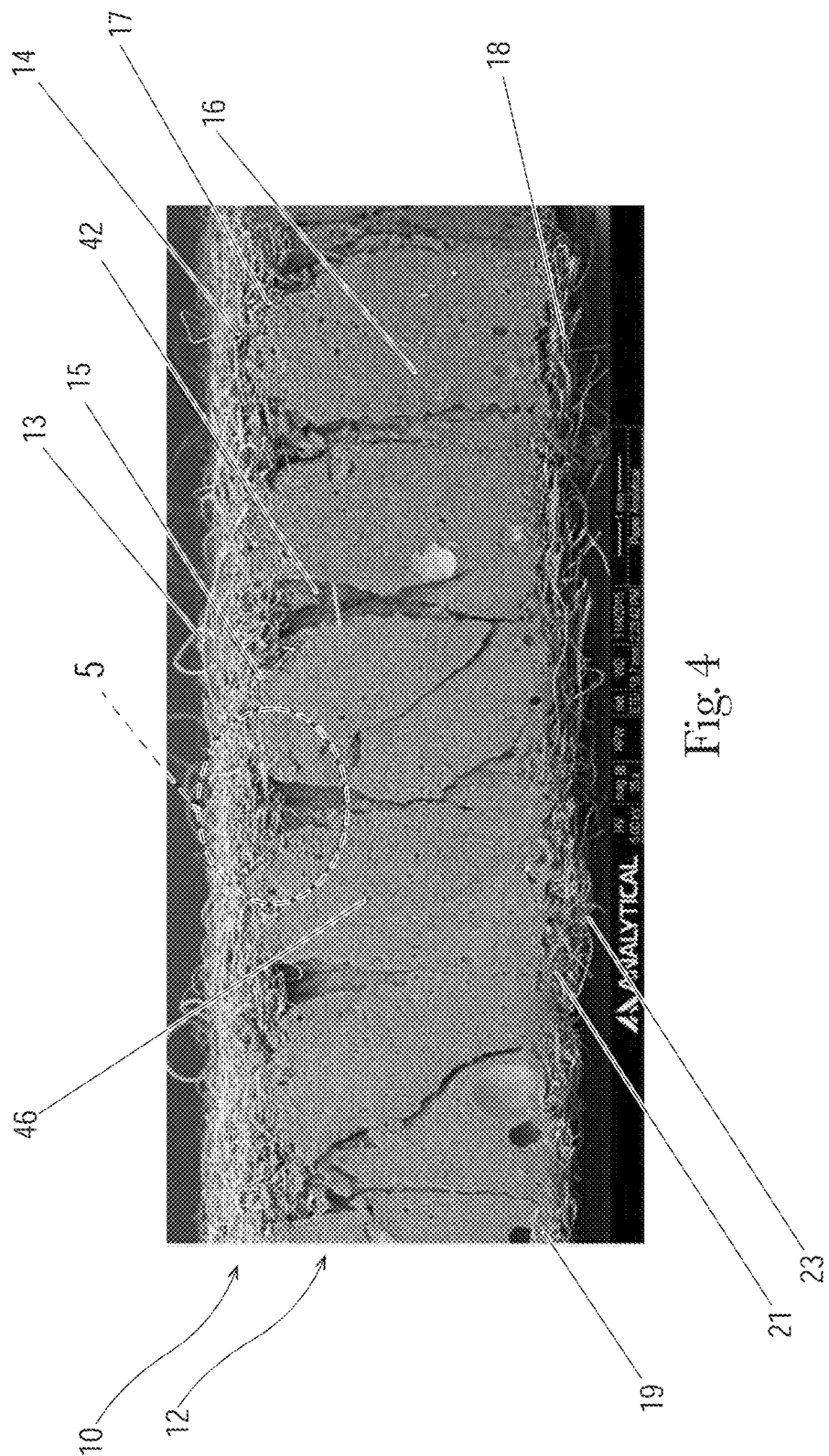
FIG. 4 is an SEM of a cross section of a fluid etched absorbent layer

FIG. 4 is an SEM of a fluid etched absorbent structure 10 in the form of a heterogeneous stratum layer 12. As shown in the figure taken at a magnification of 35×, the fluid has penetrated through the first fibrous layer 14 and into the foam layer 16. As shown in the figure, the fluid has not penetrated the second fibrous layer 18. As shown in the image, the use of the fluid etching allows one to leave unchanged sections 46. The layer exemplified in FIG. 4 was created using a small hole stencil. The stencil allowed for an decreased amount of fluid to penetrate the layer during the residence time spent under the fluid jet creating fissures 42 in the absorbent stratum 12. As shown in the figure, the fluid only removed foam from a portion of the top half of the stratum layer 12. The removed foam has been removed from the desired areas without damaging the foam below or the fibrous network above and below the foam which remain substantially planar. As shown in the figure, a portion of the second layer 16 first surface 17 enrobes a portion of the first fibrous layer 14 second surface 15. Additionally, a portion of the second layer 16 second surface 19 enrobes a portion of the second fibrous layer 18 first surface 21.

Figure 5:
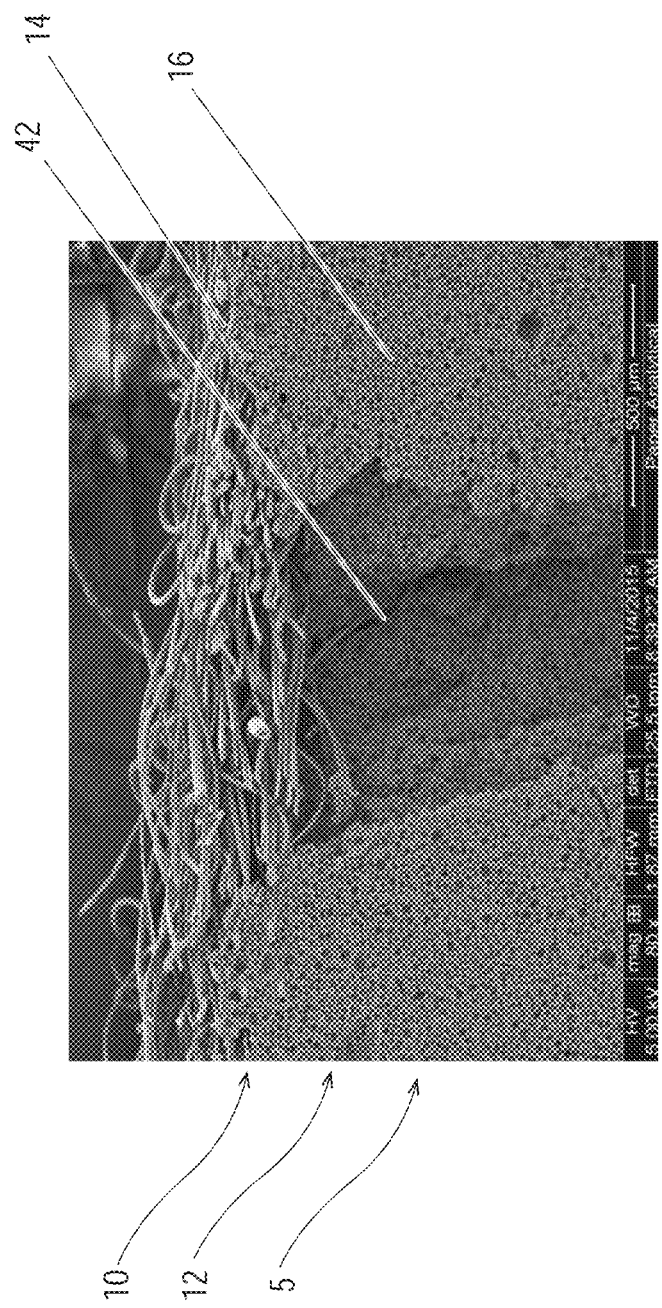
FIG. 5 is an enlarged view of a portion of the web shown in FIG. 4.

FIG. 5 is a zoomed in view of a portion of FIG. 4. The figure shows a portion of the first fibrous layer 14 and the foam layer 16 of an absorbent structure 10. As shown in the figure, a fissure 42 has been etched into the foam layer 16.

FIG. 6 is a top view of a fluid etched heterogeneous stratum 12 created with back lighting. As shown in the image, by selectively etching the absorbent structure 10 one may create intricate designs and patterns that are both functional and aesthetically pleasing.

Once the fluid etched material is manufactured in accordance with the present disclosure it may be incorporated into, for example, an absorbent material.

Referring to FIG. 7, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

With regard to the sanitary napkin 110 of FIG. 7, the secondary topsheet 20 incorporating the fluid etched stratum of heterogeneous mass may be bonded to, or otherwise attached to the topsheet 114. In some embodiments, thermal point calendaring or other suitable bonding is utilized. In other embodiments, the fluid etched stratum of heterogeneous mass may serve as an absorbent core of an absorbent article. The fluid etched stratum of heterogeneous mass may serve as the topsheet for an absorbent article, the secondary topsheet of an absorbent article. Additionally, an absorbent article may utilize two or more fluid etched stratums of heterogeneous masses within one absorbent article. For example, panty liners and incontinence pads may be formed with the fluid etched stratum of heterogeneous mass positioned between a topsheet and a bottom sheet to function as an absorbent core. Furthermore the fluid etched absorbent structure having a first layer and a second layer may not include a binder component.

The sanitary napkin 110 may have any shape known in the art for feminine hygiene articles, including the generally symmetric "hourglass" shape, as well as pear shapes, bicycle-seat shapes, trapezoidal shapes, wedge shapes or other shapes that have one end wider than the other.

The topsheet 114, the backsheet 116, and the absorbent core 118 may be assembled in a variety of well-known configurations, including so called "tube" products or side flap products, such as, for example, configurations are described generally in U.S. Pat. No. 4,950,264, "Thin, Flexible Sanitary Napkin" issued to Osborn on Aug. 21, 1990, U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, and "Shaped Sanitary Napkin With Flaps" issued to Van Tilburg on Aug. 18, 1987. Each of these patents is incorporated herein by reference.

Figure 9:
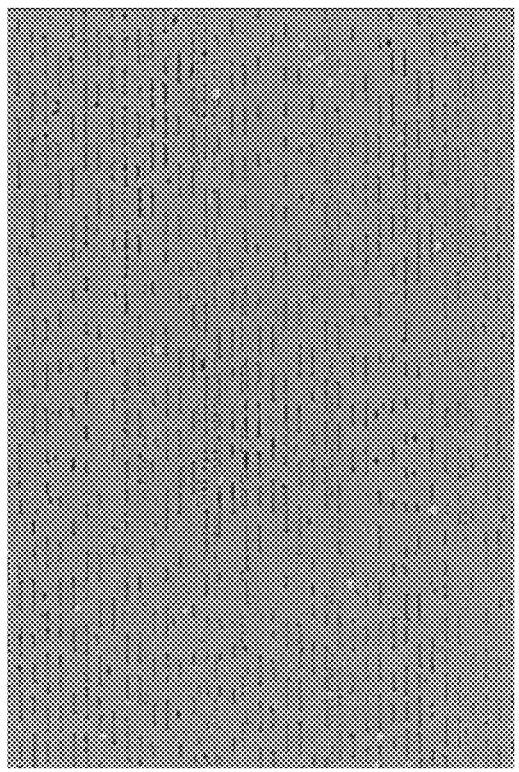
FIG. 9 is a top view of the structure of FIG. 8 with a backlight.
Figure 10:
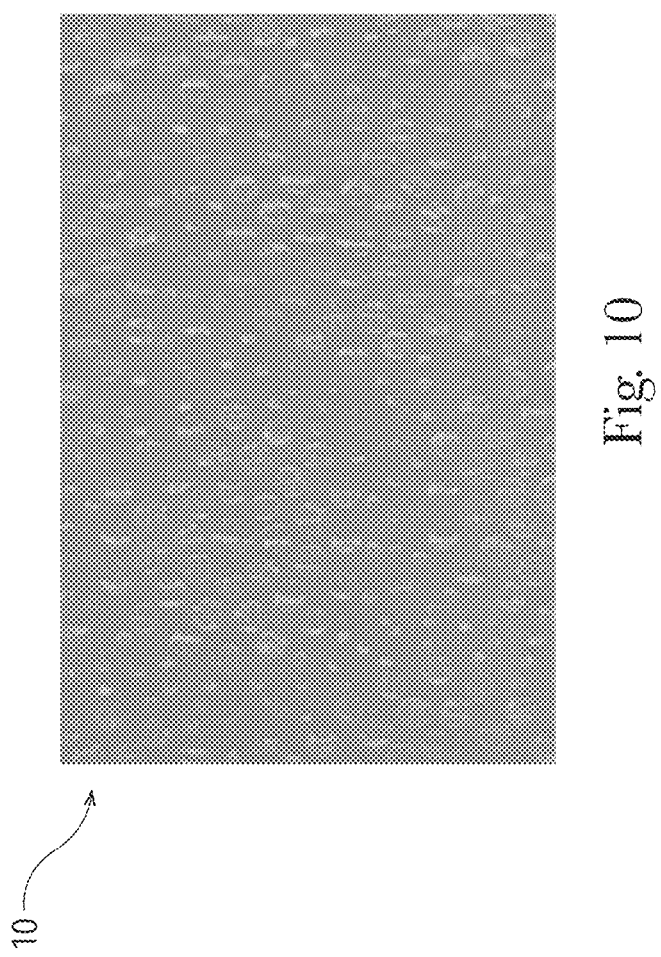
FIG. 10 is a top view of a fluid etched absorbent structure.
Figure 12:
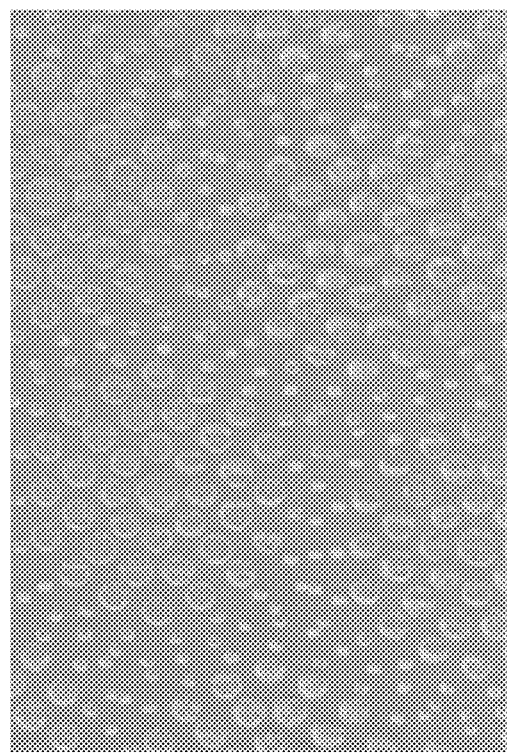
FIG. 12 is a top view of a fluid etched absorbent structure.
Figure 13:
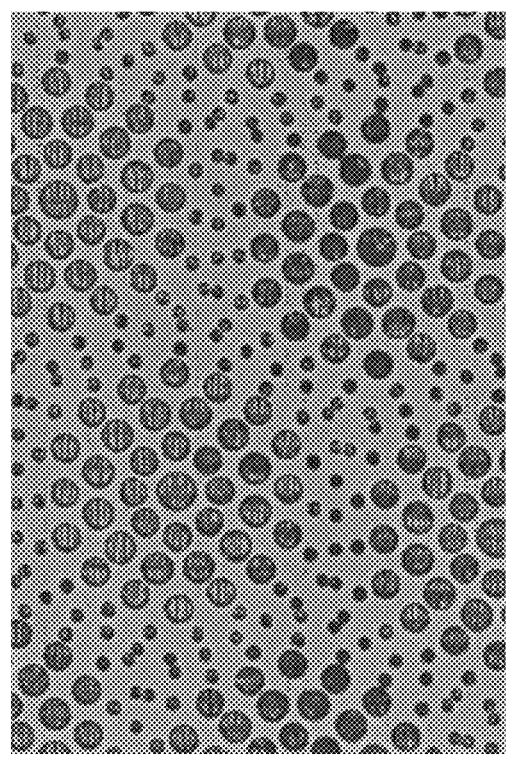
FIG. 13 is a top view of the structure of FIG. 12 with a backlight.

FIGS. 8-12 represent potential patterns that may be created in an absorbent structure 10 utilizing a fluid etching system. FIGS. 8, 10, and 12 represent images of the etched patterns with no backlight behind the absorbent structure. FIG. 9 represent the pattern of FIG. 8 with a backlight. FIG. 11 represents the pattern of FIG. 10 with a backlight. FIG. 13 represents the pattern of FIG. 12 with a backlight. The pattern of FIGS. 8/9 was created under 75 bar fluid pressure at a rate of 5 m/min with a target of 10 holes/inch. The pattern of FIGS. 10/11 was created under 50 bar fluid pressure at a rate of 5 m/min with a target of 40 holes/inch. The pattern of FIGS. 12/13 was created under 200 bar fluid pressure at a rate of 5 m/min with a target of 40 holes/inch.

Following polymerization, the resulting foam pieces are saturated with aqueous phase that needs to be removed to obtain substantially dry foam pieces. In certain embodiments, foam pieces may be squeezed free of most of the aqueous phase by using compression, for example by running the heterogeneous mass comprising the foam pieces through one or more pairs of nip rollers. The nip rollers may be positioned such that they squeeze the aqueous phase out of the foam pieces. The nip rollers may be porous and have a vacuum applied from the inside such that they assist in drawing aqueous phase out of the foam pieces. In certain embodiments, nip rollers may be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller may be pressurized while the other, for example the second nip roller, may be evacuated, so as to both blow and draw the aqueous phase out the of the foam. The nip rollers may also be heated to assist in removing the aqueous phase. In certain embodiments, nip rollers are only applied to non-rigid foams, that is, foams whose walls would not be destroyed by compressing the foam pieces.

In certain embodiments, in place of or in combination with nip rollers, the aqueous phase may be removed by sending the foam pieces through a drying zone where it is heated, exposed to a vacuum, or a combination of heat and vacuum exposure. Heat may be applied, for example, by running the foam though a forced air oven, IR oven, microwave oven or radiowave oven. The extent to which a foam is dried depends on the application. In certain embodiments, greater than 50% of the aqueous phase is removed. In certain other embodiments greater than 90%, and in still other embodiments greater than 95% of the aqueous phase is removed during the drying process.

In an embodiment, open-cell foam is produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photo-initiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking co-monomer, or cross-linker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of cross-linkers contain a mixture of acrylate and methacrylate moieties, such as ethylene glycol acrylate-methacrylate and neopentyl glycol acrylate-methacrylate. The ratio of methacrylate:acrylate group in the mixed cross-linker may be varied from 50:50 to any other ratio as needed.

Any third substantially water-insoluble co-monomer may be added to the oil phase in weight percentages of from about 0% to about 15% by weight of the oil phase, in certain embodiments from about 2% to about 8%, to modify properties of the HIPE foams. In certain embodiments, "toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers may be used to slow down the polymerization rate of a HIPE. Examples of monomers of this type may have styrene and vinyl chloride.

The oil phase may further contain an emulsifier used for stabilizing the HIPE. Emulsifiers used in a HIPE may include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they may have between about 1% and about 20%, in certain embodiments from about 2% to about 15%, and in certain other embodiments from about 3% to about 12% by weight of the oil phase. In certain embodiments, co-emulsifiers may also be used to provide additional control of cell size, cell size distribution, and emulsion stability, particularly at higher temperatures, for example greater than about 65° C. Examples of co-emulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts.

In certain embodiments, ditallow dimethyl ammonium methyl sulfate (DTDMAMS) may be used as a co-emulsifier.

The oil phase may comprise a photo-initiator at between about 0.05% and about 10%, and in certain embodiments between about 0.2% and about 10% by weight of the oil phase. Lower amounts of photo-initiator allow light to better penetrate the HIPE foam, which may provide for polymerization deeper into the HIPE foam. However, if polymerization is done in an oxygen-containing environment, there should be enough photo-initiator to initiate the polymerization and overcome oxygen inhibition. Photo-initiators may respond rapidly and efficiently to a light source with the production of radicals, cations, and other species that are capable of initiating a polymerization reaction. The photo-initiators used in the present invention may absorb UV light at wavelengths of about 200 nanometers (nm) to about 800 nm, in certain embodiments about 200 nm to about 350 nm. If the photo-initiator is in the oil phase, suitable types of oil-soluble photo-initiators include benzyl ketals, α-hydroxyalkyl phenones, α-amino alkyl phenones, and acylphospine oxides. Examples of photo-initiators include 2,4,6-[trimethylbenzoyldiphosphine]oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio) phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl) phenyl]propanone] (sold by Lambeth spa, Gallarate, Italy as ESACURE® KIP EM.

The dispersed aqueous phase of a HIPE may have water, and may also have one or more components, such as initiator, photo-initiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, co-monomers, and cross-linkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte may include a buffering agent for the control of pH during the polymerization, including such inorganic counter-ions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator may be present at up to about 20 mole percent based on the total moles of polymerizable monomers present in the oil phase. In certain embodiments, the initiator is present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine) dihydrochloride, and other suitable azo initiators. In certain embodiments, to reduce the potential for premature polymerization which may clog the emulsification system, addition of the initiator to the monomer phase may be just after or near the end of emulsification.

Photo-initiators present in the aqueous phase may be at least partially water soluble and may have between about 0.05% and about 10%, and in certain embodiments between about 0.2% and about 10% by weight of the aqueous phase. Lower amounts of photo-initiator allow light to better penetrate the HIPE foam, which may provide for polymerization deeper into the HIPE foam. However, if polymerization is done in an oxygen-containing environment, there should be enough photo-initiator to initiate the polymerization and overcome oxygen inhibition. Photo-initiators may respond rapidly and efficiently to a light source with the production of radicals, cations, and other species that are capable of initiating a polymerization reaction. The photo-initiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photo-initiator is in the aqueous phase, suitable types of water-soluble photo-initiators include benzophenones, benzils, and thioxanthones. Examples of photo-initiators include 2,2'-Azobis[2-(2-imidazolin-2-yl)propane] dihydrochloride; 2,2'-Azobis[2-(2-imidazolin-2-yl)propane] disulfate dehydrate; 2,2'-Azobis(1-imino-1-pyrrolidino-2-ethylpropane) dihydrochloride; 2,2'-Azobis[2-methyl-N-(2-hydroxyethyl)propionamide]; 2,2'-Azobis(2-methylpropionamidine) dihydrochloride; 2,2'-dicarboxymethoxydibenzalacetone, 4,4'-dicarboxymethoxydibenzalacetone, 4,4'-dicarboxymethoxydibenzalcyclohexanone,4-dimethylamino-4'-carboxymethoxydibenzalacetone; and 4,4'-disulphoxymethoxydibenzalacetone. Other suitable photo-initiators that may be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The fluid etchable absorbent structure may have a layer having enrobeable elements. The absorbent structure may have more than one layer having enrobeable elements. The enrobeable elements may be a web or a portion of a web such as, for example, nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof. The absorbent structure may have more than one layer having enrobeable elements.

The enrobeable elements may be, for example, conventional absorbent materials such as creped cellulose wadding, fluffed cellulose fibers, wood pulp fibers also known as airfelt, and textile fibers. The enrobeable elements may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The enrobeable elements may be any combination of the materials listed above and/or a plurality of the materials listed above, alone or in combination.

The enrobeable elements may be hydrophobic or hydrophilic. In an embodiment, the enrobeable elements may be treated to be made hydrophobic. In an embodiment, the enrobeable elements may be treated to become hydrophilic.

The constituent fibers of the heterogeneous mass may be comprised of polymers such as polyethylene, polypropylene, polyester, and blends thereof. The fibers may be spunbond fibers. The fibers may be meltblown fibers. The fibers may comprise cellulose, rayon, cotton, or other natural materials or blends of polymer and natural materials. The fibers may also comprise a super absorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers may range from about 0.1 denier to about 100 denier.

The heterogeneous mass may be comprised of more than one nonwoven precursor web. For example, the high internal phase emulsion is applied to the top surface of the first nonwoven web by means of an extrusion die in a horizontal configuration. A second nonwoven web may be applied to the top surface of the previously extruded high internal phase emulsion while in a horizontal configuration prior to the onset of solidification of the HIPE into a HIPE foam. The above described structure creates a two nonwoven structure with HIPE foam in between the nonwovens and enrobed elements at the interface of HIPE foam and nonwoven, e.g. an absorbent stratum that is a heterogeneous mass comprising a first nonwoven having a first surface and a second surface and a second nonwoven. An open cell foam piece enrobes a portion of the first nonwoven and a portion of the second nonwoven. Alternatively, the second precursor web may be glued to the stratum heterogeneous mass after polymerization of the stratum.

It has been surprisingly found that by creating a heterogenous mass layer comprising open cell foam wherein at least a portion of one or more open cell foam pieces is in contact with a substrate or layer of enrobeable elements such as nonwoven fibers at both the top and bottom surface of the piece along a vertical axis allows for the heterogeneous mass to be submitted through a fluid etching process while maintaining the fluid connectivity of the heterogeneous mass layer.

In one aspect, known absorbent web materials in an as-made may be considered as being homogeneous throughout. Being homogeneous, the fluid handling properties of the absorbent web material are not location dependent, but are substantially uniform at any area of the web. Homogeneity may be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling and or mechanical properties of the web material are location dependent. Therefore, for the heterogeneous absorbent materials of the present invention, at discrete locations the density or basis weight of the web may be substantially different than the average density or basis weight for the web. The heterogeneous nature of the absorbent web of the present invention permits the negative aspects of either of permeability or capillarity to be minimized by rendering discrete portions highly permeable and other discrete portions to have high capillarity. Likewise, the tradeoff between permeability and capillarity is managed such that delivering relatively higher permeability may be accomplished without a decrease in capillarity. Likewise the heterogeneous nature of the absorbent web may also enable discrete bending, compression or stretch zones within the web.

In an embodiment, the heterogeneous mass may also include superabsorbent material that imbibe fluids and form hydrogels. These materials are typically capable of absorbing large quantities of body fluids and retaining them under moderate pressures and may be in either a fibrous, particulate or other physical form. The heterogeneous mass may include such materials dispersed in a suitable carrier such as cellulose fibers in the form of fluff or stiffened fibers or integrated within an AGM containing laminate.

The heterogeneous mass may include one or more types of fibers. Fibers included in the fibrous web may be thermoplastic particulates or fibers. The materials, and in particular thermoplastic fibers, may be made from a variety of thermoplastic polymers including polyolefins such as polyethylene (e.g., PULPEX®) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g. per sq. of centimeter of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e. unbent) or crimped (i.e. bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long, preferably from about 2.5 mm to about 7.5 mm long, and most preferably from about 3.0 mm to about 6.0 mm long. The properties-of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20, preferably from about 1.4 to about 10, and most preferably from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The heterogeneous mass may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, preferably from about 0.9 to about 1.5 cm. Suitable nonbonding thermoplastic fibers may have a decitex in the range of about 1.5 to about 35 decitex, more preferably from about 14 to about 20 decitex.

However structured, the total absorbent capacity of the absorbent core should be compatible with the design loading and the intended use of the mass. For example, when used in an absorbent article, the size and absorbent capacity of the heterogeneous mass may be varied to accommodate different uses such as incontinence pads, panty liners, regular sanitary napkins, or overnight sanitary napkins.

The heterogeneous mass may also include other optional components sometimes used in absorbent webs. For example, a reinforcing scrim may be positioned within the respective layers, or between the respective layers, of the heterogeneous mass.

The absorbent structure produced from the present invention may be used as an absorbent core or a portion of an absorbent core in absorbent articles, such as feminine hygiene articles, for example pads, panty liners, and tampons; wound dressing; disposable diapers; incontinence articles, for example pads, adult diapers; homecare articles, for example wipes, pads, towels; and beauty care articles, for example pads, wipes, and skin care articles, such as used for pore cleaning. The absorbent structure having a topsheet and/or a secondary topsheet integrated into a heterogeneous mass layer having open-cell foam pieces may be used in absorbent articles such as feminine hygiene articles, for example pads, panty liners, and tampons; wound dressings; disposable diapers; incontinence articles, for example pads, adult diapers; homecare articles, for example wipes, pads, towels; and beauty care articles, for example pads, wipes, and skin care articles, such as used for pore cleaning. A diaper may be an absorbent article as disclosed in U.S. patent application Ser. No. 13/428,404, filed on Mar. 23, 2012.

The absorbent core structure may be used as an absorbent core for an absorbent article. In such an embodiment, the absorbent core may be relatively thin, less than about 5 mm in thickness, or less than about 3 mm, or less than about 1 mm in thickness. Cores having a thickness of greater than 5 mm are also contemplated herein. Thickness may be determined by measuring the thickness at the midpoint along the longitudinal centerline of the pad by any means known in the art for doing while under a uniform pressure of 0.25 psi. The absorbent core may comprise absorbent gelling materials (AGM), including AGM fibers, blood gelling agents (e.g. chitosan), quaternary salts or combinations thereof as is known in the art.

The absorbent structure may be formed or cut to a shape, the outer edges of which define a periphery.

In an embodiment, the absorbent structure may be used as a topsheet for an absorbent article. The absorbent structure may be combined with an absorbent core or may only be combined with a backsheet.

In an embodiment, the absorbent structure may be combined with any other type of absorbent layer or non-absorbent layer such as, for example, a layer of cellulose, a layer comprising superabsorbent gelling materials, a layer of absorbent airlaid fibers, a nonwoven layer, or a layer of absorbent foam, or combinations thereof. Other absorbent layers not listed are contemplated herein.

According to an embodiment, an absorbent article may comprise a liquid pervious topsheet. The topsheet suitable for use herein may comprise wovens, non-wovens, apertured webs or not aperture webs, and/or three-dimensional webs of a liquid impermeable polymeric film comprising liquid permeable apertures. The topsheet for use herein may be a single layer or may have a multiplicity of layers. For example, the wearer-facing and contacting surface may be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. Nos. 3,929,135, 4,151,240, 4,319,868, 4,324,426, 4,343,314, 4,591,523, 4,609,518, 4,629,643, 4,695,422 or WO 96/00548.

The topsheet and/or the secondary topsheet may comprise a nonwoven material. The nonwoven materials of the present invention may be made of any suitable nonwoven materials ("precursor materials"). The nonwoven webs may be made from a single layer, or multiple layers (e.g., two or more layers). If multiple layers are used, they may be comprised of the same type of nonwoven material, or different types of nonwoven materials. In some cases, the precursor materials may be free of any film layers.

The fibers of the nonwoven precursor material(s) for the topsheet, the secondary topsheet, and/or the heterogeneous mass may be made of any suitable materials including, but not limited to natural materials, synthetic materials, and combinations thereof. Suitable natural materials include, but are not limited to cellulose, cotton linters, bagasse, wool fibers, silk fibers, etc. Cellulose fibers may be provided in any suitable form, including but not limited to individual fibers, fluff pulp, cotton, hemp, drylap, liner board, etc. Suitable synthetic materials include, but are not limited to nylon, rayon, and polymeric materials. Suitable polymeric materials include, but are not limited to: polyethylene (PE), polyester, polyethylene terephthalate (PET), polypropylene (PP), and co-polyester. Suitable synthetic fibers may have submicron diameters such as Nufibers or be between 1 and 3 microns such as meltblown fibers or may be of larger diameter. In some embodiments, however, the nonwoven precursor materials may be either substantially, or completely free, of one or more of these materials. For example, in some embodiments, the precursor materials may be substantially free of cellulose, and/or exclude paper materials. In some embodiments, one or more precursor materials may comprise up to 100% thermoplastic fibers. The fibers in some cases may, therefore, be substantially non-absorbent. In some embodiments, the nonwoven precursor materials may be either substantially, or completely free, of tow fibers.

The precursor nonwoven materials may comprise any suitable types of fibers. Suitable types of fibers include, but are not limited to: monocomponent, bicomponent, and/or biconstituent, non-round (e.g., shaped fibers (including but not limited to fibers having a trilobal cross-section) and capillary channel fibers). The fibers may be of any suitable size. The fibers may, for example, have major cross-sectional dimensions (e.g., diameter for round fibers) ranging from 0.1-500 microns. Fiber size may also be expressed in denier, which is a unit of weight per length of fiber. The constituent fibers may, for example, range from about 0.1 denier to about 100 denier. The constituent fibers of the nonwoven precursor web(s) may also be a mixture of different fiber types, differing in such features as chemistry (e.g., PE and PP), components (mono- and bi-), shape (i.e. capillary channel and round) and the like.

The nonwoven precursor webs may be formed from many processes, such as, for example, air laying processes, wetlaid processes, meltblowing processes, spunbonding processes, and carding processes. The fibers in the webs may then be bonded via spunlacing processes, hydroentangling, calendar bonding, through-air bonding and resin bonding. The nonwoven precursor web or nonwoven web may be aperture with a process such as overbonding or pre-aperturing. Some of such individual nonwoven webs may have bond sites 46 where the fibers are bonded together.

In the case of spunbond webs, the web may have a thermal point bond 46 pattern that is not highly visible to the naked eye. For example, dense thermal point bond patterns are equally and uniformly spaced are typically not highly visible. After the material is processed through the mating male and female rolls, the thermal point bond pattern is still not highly visible. Alternatively, the web may have a thermal point bond pattern that is highly visible to the naked eye. For example, thermal point bonds that are arranged into a macro-pattern, such as a diamond pattern, are more visible to the naked eye. After the material is processed through the mating male and female rolls, the thermal point bond pattern is still highly visible and may provide a secondary visible texture element to the material.

The basis weight of nonwoven materials is usually expressed in grams per square meter (gsm). The basis weight of a single layer nonwoven material may range from about 5 gsm to about 400 gsm, depending on the ultimate use of the material. For example, the topsheet of a topsheet/acquisition layer laminate or composite may have a basis weight from about 8 to about 40 gsm, or from about 8 to about 30 gsm, or from about 8 to about 20 gsm. The acquisition layer may have a basis weight from about 10 to about 300 gsm, or from about 10 to about 200 gsm, or from about 10 to about 100 gsm. The basis weight of a multi-layer material is the combined basis weight of the constituent layers and any other added components. The basis weight of multi-layer materials of interest herein may range from about 20 gsm to about 150 gsm, depending on the ultimate use of the material.

The precursor nonwoven webs may have certain desired characteristics. The precursor nonwoven web(s) each have a first surface, a second surface, and a thickness. The first and second surfaces of the precursor nonwoven web(s) may be generally planar. It is typically desirable for the precursor nonwoven web materials to have extensibility to enable the fibers to stretch and/or rearrange into the form of the protrusions. If the nonwoven webs are comprised of two or more layers, it may be desirable for all of the layers to be as extensible as possible. Extensibility is desirable in order to maintain at least some non-broken fibers in the sidewalls around the perimeter of the protrusions. It may be desirable for individual precursor webs, or at least one of the nonwovens within a multi-layer structure, to be capable of undergoing an apparent elongation (strain at the breaking force, where the breaking force is equal to the peak force) of greater than or equal to about one of the following amounts: 100% (that is double its unstretched length), 110%, 120%, or 130% up to about 200%. It is also desirable for the precursor nonwoven webs to be capable of undergoing plastic deformation to ensure that the structure of the deformations is "set" in place so that the nonwoven web will not tend to recover or return to its prior configuration.

Materials that are not extensible enough (e.g., inextensible PP) may form broken fibers around much of the perimeter of the deformation, and create more of a "hanging chad" (i.e., the cap of the protrusions may be at least partially broken from and separated from the rest of the protrusion. The area on the sides of the protrusion where the fibers are broken is designated with reference number.

When the fibers of a nonwoven web are not very extensible, it may be desirable for the nonwoven to be underbonded as opposed to optimally bonded. A thermally bonded nonwoven web's tensile properties may be modified by changing the bonding temperature. A web may be optimally or ideally bonded, underbonded, or overbonded. Optimally or ideally bonded webs are characterized by the highest breaking force and apparent elongation with a rapid decay in strength after reaching the breaking force. Under strain, bond sites fail and a small amount of fibers pull out of the bond site. Thus, in an optimally bonded nonwoven, the fibers will stretch and break around the bond sites when the nonwoven web is strained beyond a certain point. Often there is a small reduction in fiber diameter in the area surrounding the thermal point bond sites. Underbonded webs have a lower breaking force and apparent elongation when compared to optimally bonded webs, with a slow decay in strength after reaching the breaking force. Under strain, some fibers will pull out from the thermal point bond sites. Thus, in an underbonded nonwoven, at least some of the fibers may be separated easily from the bond sites to allow the fibers to pull out of the bond sites and rearrange when the material is strained. Overbonded webs also have a lowered breaking force and elongation when compared to optimally bonded webs, with a rapid decay in strength after reaching the breaking force. The bond sites look like films and result in complete bond site failure under strain.

When the nonwoven web comprises two or more layers, the different layers may have the same properties, or any suitable differences in properties relative to each other. In one embodiment, the nonwoven web may comprise a two layer structure that is used in an absorbent article. For convenience, the precursor webs and the material into which they are formed will generally be referred to herein by the same reference numbers. As described above, one of the layers, a second layer, may serve as the topsheet of the absorbent article, and the first layer may be an underlying layer (or sub-layer) and serve as an acquisition layer. The acquisition layer receives liquids that pass through the topsheet and distributes them to underlying absorbent layers. In such a case, the topsheet may be less hydrophilic than sub-layer(s), which may lead to better dewatering of the topsheet. In other embodiments, the topsheet may be more hydrophilic than the sub-layer(s). In some cases, the pore size of the acquisition layer may be reduced, for example via using fibers with smaller denier or via increasing the density of the acquisition layer material, to better dewater the pores of the topsheet.

The second nonwoven layer that may serve as the topsheet or secondary topsheet may have any suitable properties. Properties of interest for the second nonwoven layer, when it serves as a topsheet, in addition to sufficient extensibility and plastic deformation may include uniformity and opacity. As used herein, "uniformity" refers to the macroscopic variability in basis weight of a nonwoven web. As used, herein, "opacity" of nonwoven webs is a measure of the impenetrability of visual light, and is used as visual determination of the relative fiber density on a macroscopic scale. As used herein, "opacity" of the different regions of a single nonwoven deformation is determined by taking a photomicrograph at 20× magnification of the portion of the nonwoven containing the deformation against a black background. Darker areas indicate relatively lower opacity (as well as lower basis weight and lower density) than white areas.

Several examples of nonwoven materials suitable for use as the second nonwoven layer include, but are not limited to: spunbonded nonwovens; carded nonwovens; and other nonwovens with high extensibility (apparent elongation in the ranges set forth above) and sufficient plastic deformation to ensure the structure is set and does not have significant recovery. One suitable nonwoven material as a topsheet for a topsheet/acquisition layer composite structure may be an extensible spunbonded nonwoven comprising polypropylene and polyethylene. The fibers may comprise a blend of polypropylene and polyethylene, or they may be bi-component fibers, such as a sheath-core fiber with polyethylene on the sheath and polypropylene in the core of the fiber. Another suitable material is a bi-component fiber spunbonded nonwoven comprising fibers with a polyethylene sheath and a polyethylene/polypropylene blend core.

The first nonwoven layer that may, for example, serve as the acquisition layer may have any suitable properties. Properties of interest for the first nonwoven layer, in addition to sufficient extensibility and plastic deformation may include uniformity and opacity. If the first nonwoven layer serves as an acquisition layer, its fluid handling properties must also be appropriate for this purpose. Such properties may include: permeability, porosity, capillary pressure, caliper, as well as mechanical properties such as sufficient resistance to compression and resiliency to maintain void volume. Suitable nonwoven materials for the first nonwoven layer when it serves as an acquisition layer include, but are not limited to: spunbonded nonwovens; through-air bonded ("TAB") carded nonwoven materials; spunlace nonwovens; hydroentangled nonwovens; and, resin bonded carded nonwoven materials. Of course, the composite structure may be inverted and incorporated into an article in which the first layer serves as the topsheet and the second layer serves as an acquisition layer. In such cases, the properties and exemplary methods of the first and second layers described herein may be interchanged.

The layers of a two or more layered nonwoven web structure may be combined together in any suitable manner. In some cases, the layers may be unbonded to each other and held together autogenously (that is, by virtue of the formation of deformations therein). For example, both precursor webs and contribute fibers to deformations in a "nested" relationship that joins the two precursor webs together, forming a multi-layer web without the use or need for adhesives or thermal bonding between the layers. In other embodiments, the layers may be joined together by other mechanisms. If desired an adhesive between the layers, ultrasonic bonding, chemical bonding, resin or powder bonding, thermal bonding, or bonding at discrete sites using a combination of heat and pressure may be selectively utilized to bond certain regions or all of the precursor webs. In addition, the multiple layers may be bonded during processing, for example, by carding one layer of nonwoven onto a spunbond nonwoven and thermal point bonding the combined layers. In some cases, certain types of bonding between layers may be excluded. For example, the layers of the present structure may be non-hydroentangled together.

If adhesives are used, they may be applied in any suitable manner or pattern including, but not limited to: slots, spirals, spray, and curtain coating. Adhesives may be applied in any suitable amount or basis weight including, but not limited to between about 0.5 and about 30 gsm, alternatively between about 2 and about 5 gsm. Examples of adhesives could include hot melt adhesives, such as polyolefins and styrene block copolymers.

A certain level of adhesive may reduce the level of fuzz on the surface of the nonwoven material even though there may be a high percentage of broken fibers as a result of the deformation process. Glued dual-layer laminates produced as described herein are evaluated for fuzz. The method utilizes a Martindale Abrasion Tester, based upon ASTM D4966-98. After abrading the samples, they are graded on a scale of 1-10 based on the degree of fiber pilling (1=no fiber pills; 10=large quantity and size of fiber pills). The protrusions are oriented away from the abrader so the land area in between the depressions is the primary surface abraded. Even though the samples may have a significant amount of fiber breakage (greater than 25%, sometimes greater than 50%) in the side walls of the protrusions/depressions, the fuzz value may be low (around 2) for several different material combinations, as long as the layers do not delaminate during abrasion. Delamination is best prevented by glue basis weight, for example a glue basis weight greater than 3 gsm, and glue coverage.

When the precursor nonwoven web comprises two or more layers, it may be desirable for at least one of the layers to be continuous, such as in the form of a web that is unwound from a roll. In some embodiments, each of the layers may be continuous. In alternative embodiments, one or more of the layers may be continuous, and one or more of the layers may have a discrete length. The layers may also have different widths. For example, in making a combined topsheet and acquisition layer for an absorbent article, the nonwoven layer that will serve as the topsheet may be a continuous web, and the nonwoven layer that will serve as the acquisition layer may be fed into the manufacturing line in the form of discrete length (for example, rectangular, or other shaped) pieces that are placed on top of the continuous web. Such an acquisition layer may, for example, have a lesser width than the topsheet layer. The layers may be combined together as described above.

Nonwoven webs and materials are often incorporated into products, such as absorbent articles, at high manufacturing line speeds. Such manufacturing processes may apply compressive and shear forces on the nonwoven webs that may damage certain types of three-dimensional features that have been purposefully formed in such webs. In addition, in the event that the nonwoven material is incorporated into a product (such as a disposable diaper) that is made or packaged under compression, it becomes difficult to preserve the three-dimensional character of some types of prior three-dimensional features after the material is subjected to such compressive forces.

The nonwoven material may comprise a composite of two or more nonwoven materials that are joined together. In such a case, the fibers and properties of the first layer will be designated accordingly (e.g., the first layer is comprised of a first plurality of fibers), and the fibers and properties of the second and subsequent layers will be designated accordingly (e.g., the second layer is comprised of a second plurality of fibers). In a two or more layer structure, there are a number of possible configurations the layers may take following the formation of the deformations therein. These will often depend on the extensibility of the nonwoven materials used for the layers. It is desirable that at least one of the layers have deformations which form protrusions as described herein in which, along at least one cross-section, the width of the cap of the protrusions is greater than the width of the base opening of the deformations. For example, in a two layer structure where one of the layers will serve as the topsheet of an absorbent article and the other layer will serve as an underlying layer (such as an acquisition layer), the layer that has protrusions therein may comprise the topsheet layer. The layer that most typically has a bulbous shape will be the one which is in contact with the male forming member during the process of deforming the web.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. An absorbent article comprising a topsheet, a backsheet, and an absorbent structure, the absorbent structure comprising a first layer comprising a first surface facing away from an absorbent second layer, and a second surface facing the absorbent second layer, the absorbent second layer comprising a first surface and a second surface, wherein the first layer is substantially planar and comprises a fibrous nonwoven web and the absorbent second layer comprises a continuous layer of open cell foam having a predetermined pattern of voids therein, in which portions of the foam have been removed by fluid expelled from fluid jets directed at the absorbent structure following formation of the foam, wherein at least a portion of fibers proximate the first layer second surface are enrobed by the open cell foam, and wherein the pattern of voids is visible in both the first surface of the nonwoven web and the open cell foam.

2. The absorbent article of claim 1, wherein the first layer and the second layer are joined without use of an adhesive.

3. The absorbent article of claim 1, wherein the absorbent structure further comprises a third layer having a first surface and second surface.

4. The absorbent article of claim 3, wherein the third layer is substantially planar.

5. The absorbent article of claim 1, wherein the voids allow for bending in one of the machine direction, the cross direction, or along a vertical axis.

6. The absorbent article of claim 3, wherein the third layer comprises a nonwoven web and the open cell foam enrobes at least a portion of fibers of the third layer proximate the third layer first surface.

7. The absorbent article of claim 3, wherein the first layer and the third layer comprise the same material.

8. The absorbent article of claim 1, wherein the absorbent structure is an absorbent core for the absorbent article.

9. An absorbent article comprising a topsheet, a backsheet, and an absorbent structure, the absorbent structure comprising a first layer comprising a first surface facing away from an absorbent second layer, and a second surface facing the absorbent second layer, the absorbent second layer comprising a first surface and second surface, wherein the first layer is substantially planar and comprises a fibrous nonwoven web and the absorbent second layer comprises a continuous layer of open cell foam and having a predetermined pattern of fissures that penetrate between 1% and 99% of the second layer, in which portions of the foam have been removed by fluid expelled from fluid jets directed at the absorbent structure following formation of the foam, wherein at least a portion of fibers proximate the first layer second surface are enrobed by the open cell foam, and wherein the pattern of voids is visible in both the first surface of the nonwoven web and the open cell foam.

10. The absorbent article of claim 9, wherein the absorbent structure further comprises voids through the absorbent layer, the voids created within the foam following formation of the foam.

11. The absorbent article of claim 9, wherein the absorbent structure further comprises a third layer having a first surface and second surface.

12. The absorbent article of claim 11, wherein the third layer is substantially planar.

13. The absorbent article of claim 9, wherein the fissures allow for bending in one of the machine direction, the cross direction, or along a vertical axis.

14. The absorbent article of claim 11, wherein the third layer comprises a fibrous nonwoven web and open cell foam proximate the second layer second surface enrobes at least a portion of fibers proximate the third layer first surface.

15. The absorbent article of claim 11, wherein the first layer and the third layer comprise the same material.

16. The absorbent article of claim 9, wherein the absorbent structure is an absorbent core for the absorbent article.

* * * * *